United States Patent
Cheong et al.

(10) Patent No.: US 10,420,814 B2
(45) Date of Patent: Sep. 24, 2019

(54) COMPOSITION FOR TREATING CANCER STEM CELLS

(71) Applicant: Bio Synosia Co., Ltd., Seoul (KR)

(72) Inventors: Jae Ho Cheong, Seoul (KR); Eun Sung Park, Seoul (KR); Ki Cheong Park, Gyeonggi-do (KR)

(73) Assignee: Haimbio Co., Ltd., Seoul (KR)

( * ) Notice: Subject to any disclaimer, the term of this patent is extended or adjusted under 35 U.S.C. 154(b) by 7 days.

(21) Appl. No.: 15/522,558

(22) PCT Filed: Oct. 28, 2015

(86) PCT No.: PCT/KR2015/011436
§ 371 (c)(1),
(2) Date: Apr. 27, 2017

(87) PCT Pub. No.: WO2016/068600
PCT Pub. Date: May 6, 2016

(65) Prior Publication Data
US 2017/0312333 A1    Nov. 2, 2017

(30) Foreign Application Priority Data

Oct. 29, 2014 (KR) .................. 10-2014-0147972

(51) Int. Cl.
| | | |
|---|---|---|
| *A61K 31/351* | (2006.01) | |
| *A61P 35/00* | (2006.01) | |
| *A61K 38/10* | (2006.01) | |
| *A61K 31/70* | (2006.01) | |
| *A61K 31/455* | (2006.01) | |
| *A61K 31/155* | (2006.01) | |
| *A61K 31/7004* | (2006.01) | |

(52) U.S. Cl.
CPC .......... *A61K 38/10* (2013.01); *A61K 31/155* (2013.01); *A61K 31/351* (2013.01); *A61K 31/455* (2013.01); *A61K 31/70* (2013.01); *A61K 31/7004* (2013.01); *A61P 35/00* (2018.01)

(58) Field of Classification Search
CPC ........ A61K 38/10; A61K 31/351; A61P 35/00
See application file for complete search history.

(56) References Cited

U.S. PATENT DOCUMENTS

| | | | |
|---|---|---|---|
| 8,685,926 B2 | 4/2014 | Bayer | |
| 2004/0096898 A1* | 5/2004 | Grover | ..................... C07K 7/06 |
| | | | 435/7.1 |
| 2011/0098232 A1* | 4/2011 | Zeilig | .................... A61K 31/37 |
| | | | 514/19.2 |
| 2014/0065246 A1 | 3/2014 | Zeilig | |
| 2017/0107499 A1* | 4/2017 | Desir | ................ C12N 15/1137 |

FOREIGN PATENT DOCUMENTS

| | | | |
|---|---|---|---|
| KR | 10-2013-0004770 A | 1/2013 | |
| WO | WO-2013019058 A2 * | 2/2013 | ......... A61K 31/7004 |

OTHER PUBLICATIONS

Sahra et al., "Targeting Cancer Cell Metabolism: The Combination of Metformin and 2-Deoxyglucose Induces p53-Dependent Apoptosis in Prostate Cancer Cells", Cancer Research, 70(6):2465-2475 (2010).

Cao et al., "Glucose uptake inhibitor sensitizes cancer cells to daunorubicin and overcomes drug resistance in hypoxia", Cancer Chemotherapy and Pharmacology, 59:495-505 (2007).

Ciavardelli et al., "Breast cancer stem cells rely on fermentative glycolysis and are sensitive to 2-deoxyglucose treatment", Cell Death and Disease, 5, e1336 (2014).

Meng et al., "Berbamine Inhibits the Growth of Liver Cancer Cells and Cancer-Initiating Cells by Targeting Ca2+/Calmodulin-Dependent Protein Kinase II", Molecular Cancer Therapeutics, 12(10):2067-2077 (2013).

Mueller et al., "Combined Targeted Treatment to Eliminate Tumorigenic Cancer Stem Cells in Human Pancreatic Cancer", Gastroenterology, 137:1102-1113 (2009).

Pierotti et al., "Targeting metabolism for cancer treatment and prevention: metformin, an old drug with multi-faceted effects", Oncogene, 32:1475-1487 (2013).

\* cited by examiner

*Primary Examiner* — Theodore R. West
(74) *Attorney, Agent, or Firm* — McDonnell Boehnen Hulbert & Berghoff LLP

(57) ABSTRACT

The present invention relates to a composition for effectively treating cancer stem cells, and more specifically to a composition for treating cancer stem cells, which contains a glucose uptake inhibitor, a biguanide-based compound, and a calcium pump inhibitor. The composition of the present invention can be used as an agent of treating cancer stem cells by effectively inducing apoptosis of the cancer stem cells. Accordingly, the composition of the present invention can be used as a pharmaceutical composition capable of effectively treating various cancer stem cells to effectively inhibiting cancer recurrence and/or metastasis.

6 Claims, 28 Drawing Sheets

[FIG. 1]
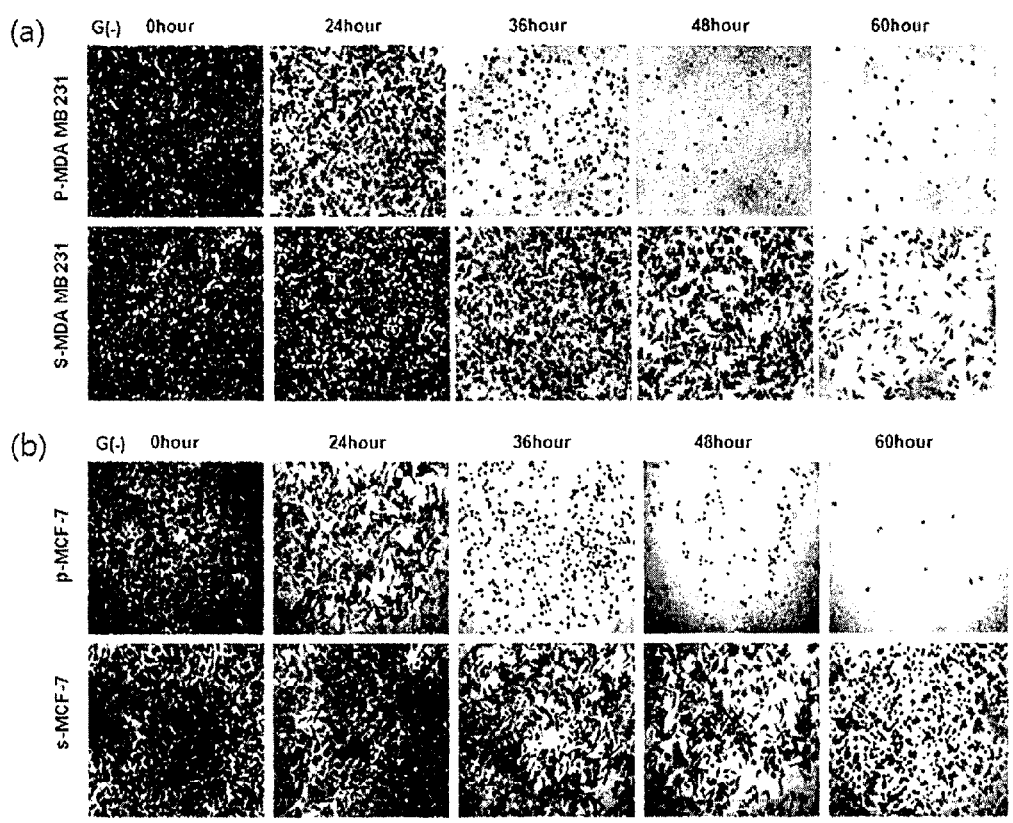

[FIG. 2]
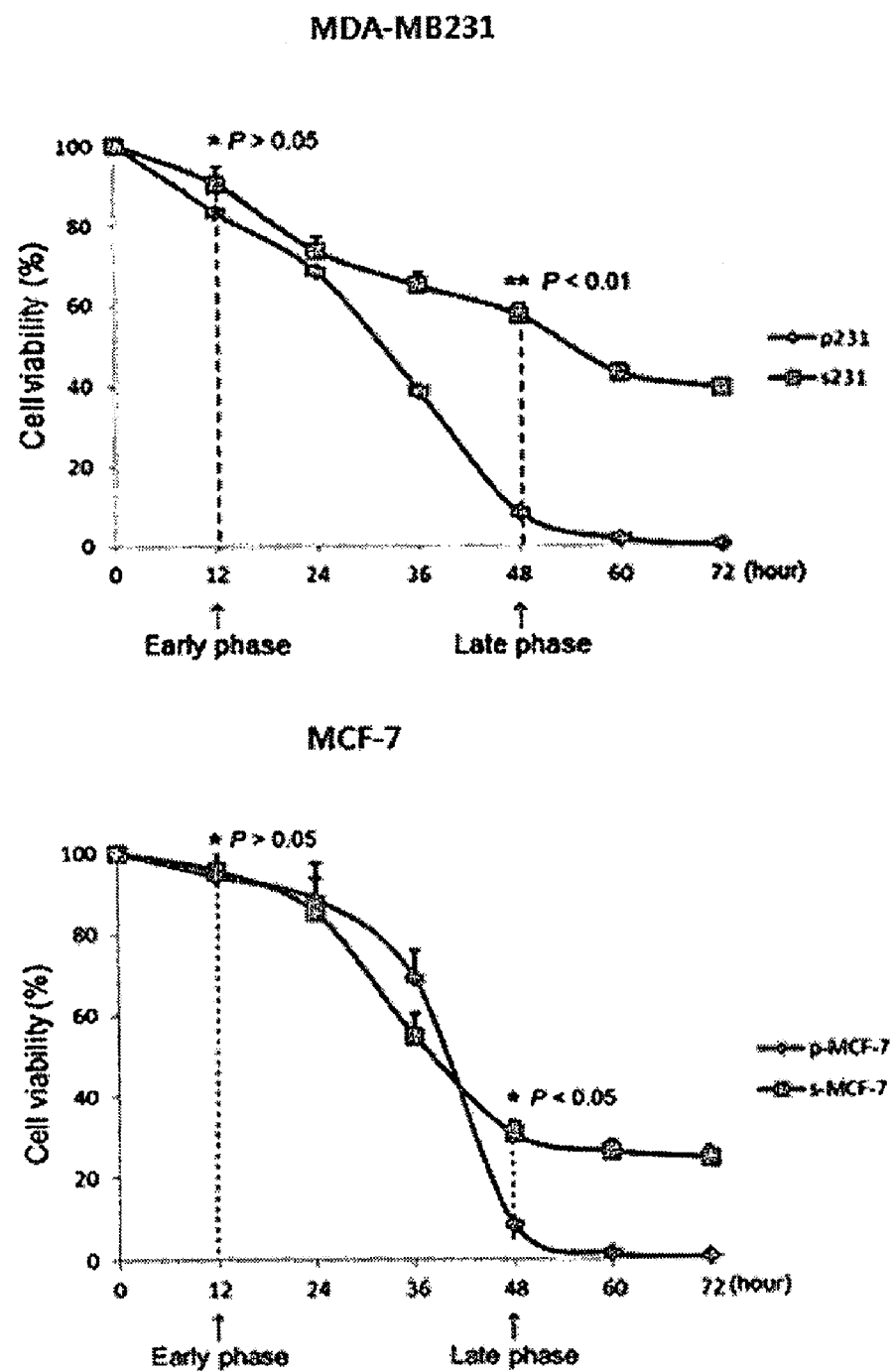

[FIG. 3]
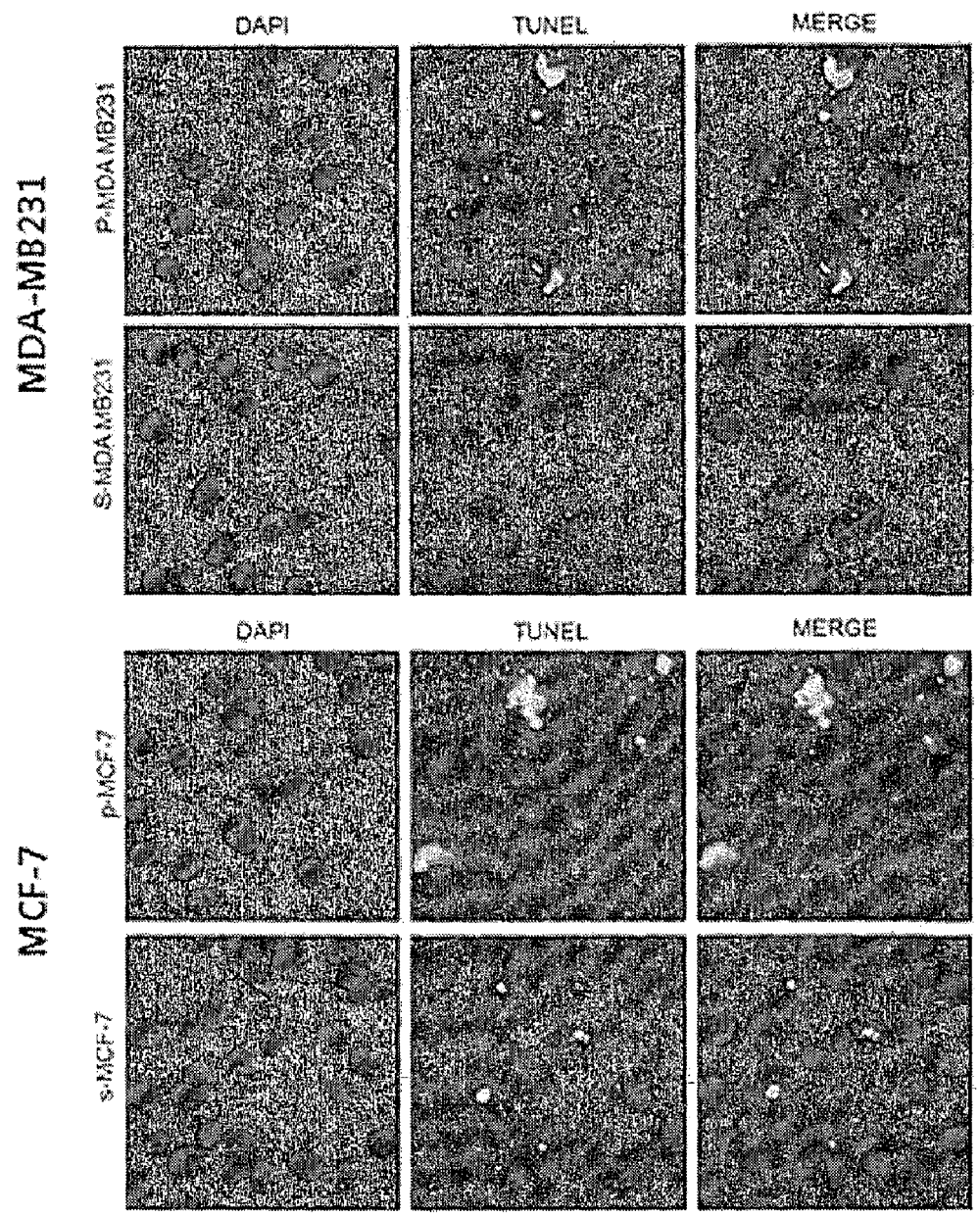

[FIG. 4]
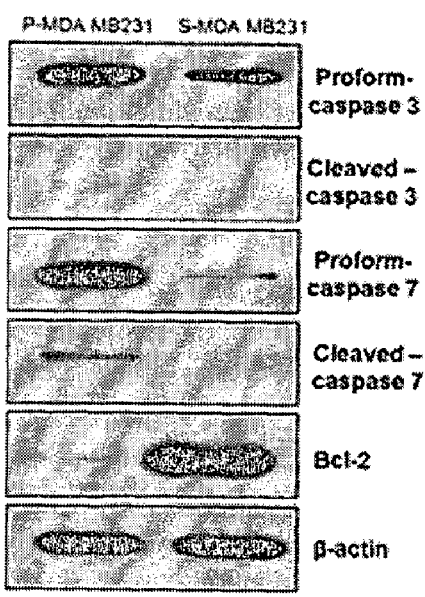
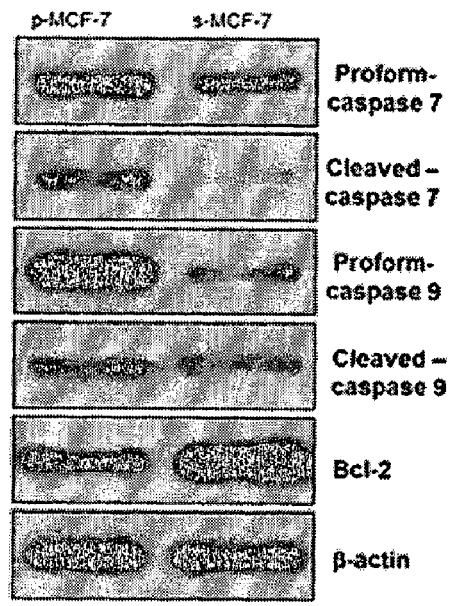

[FIG. 5]
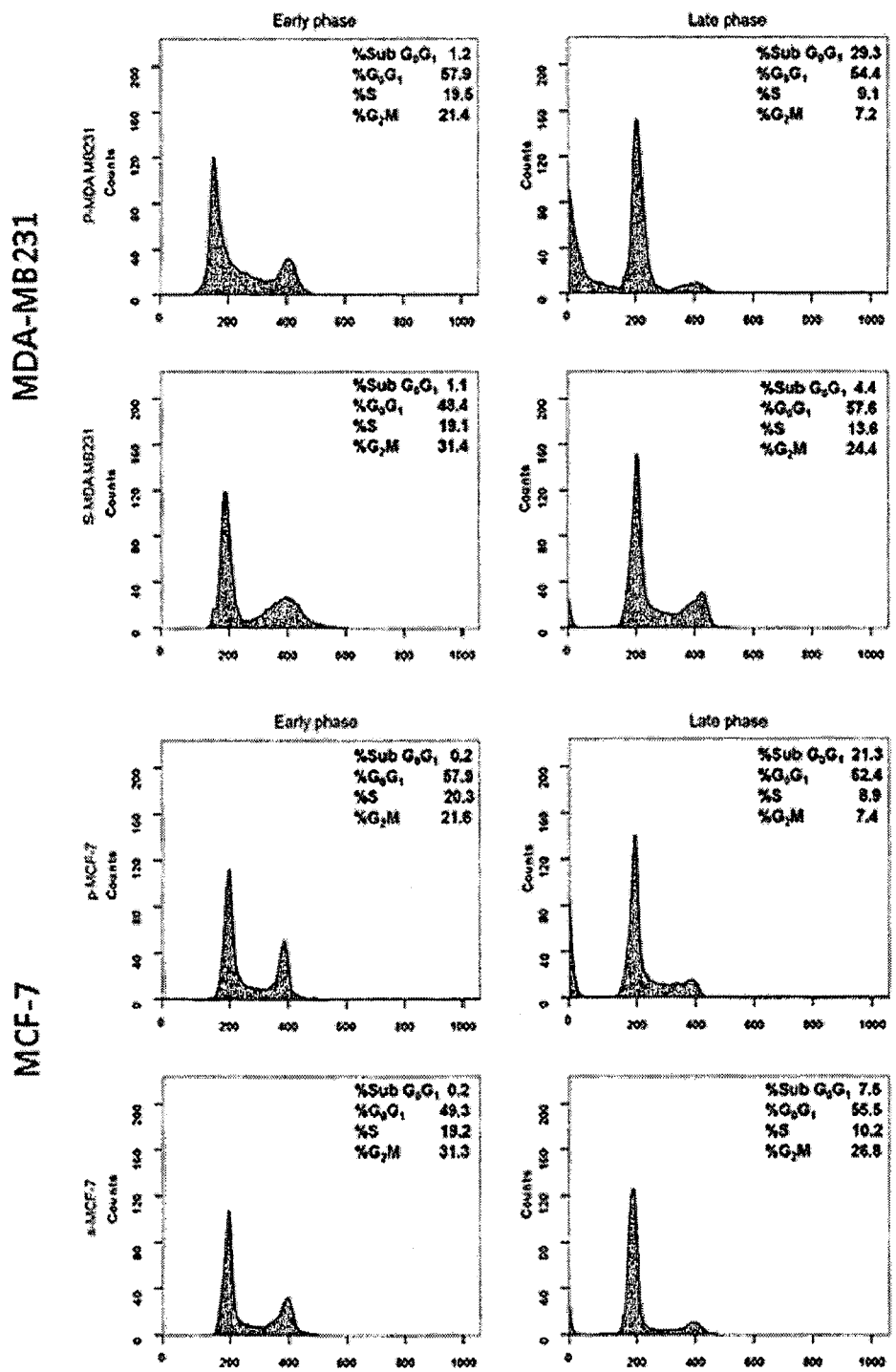

[FIG. 6]
MDA-MB231
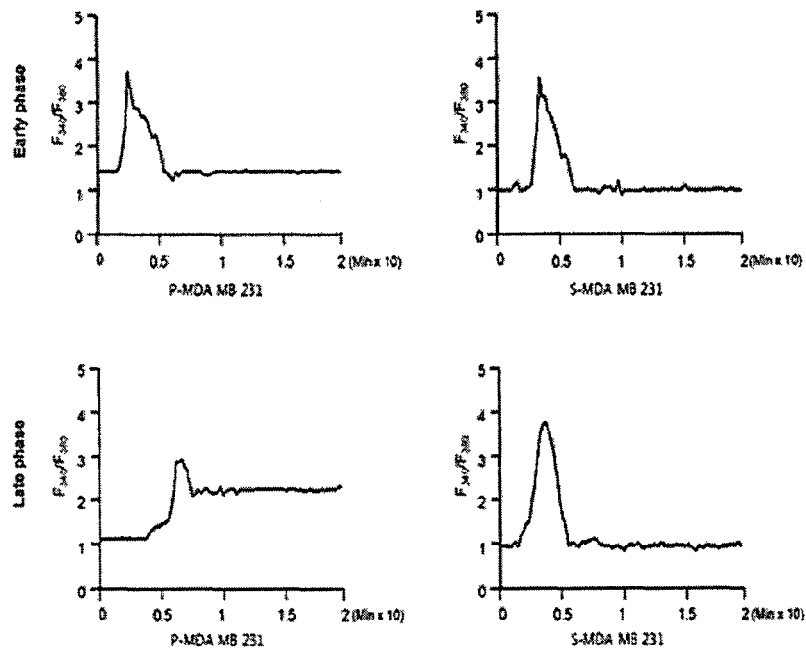
MCF-7
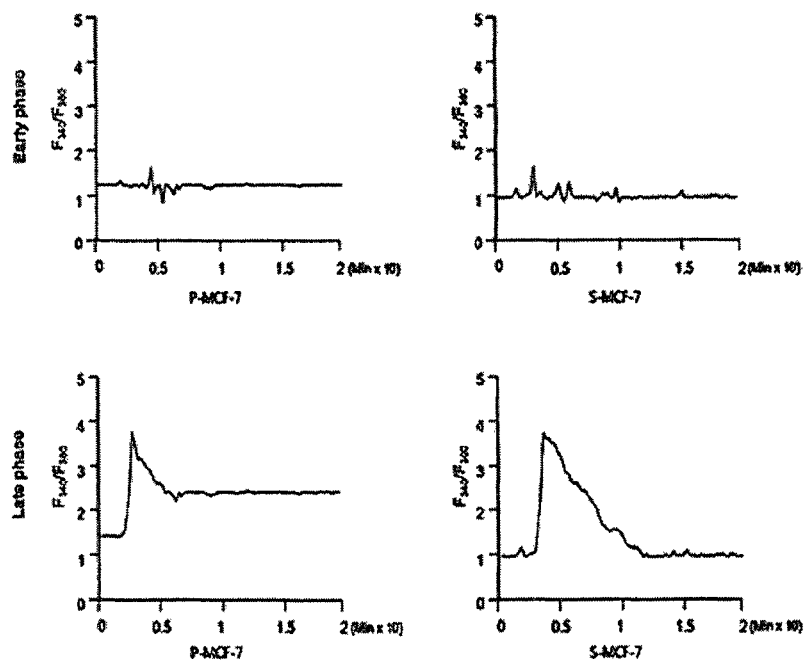

[FIG. 7]
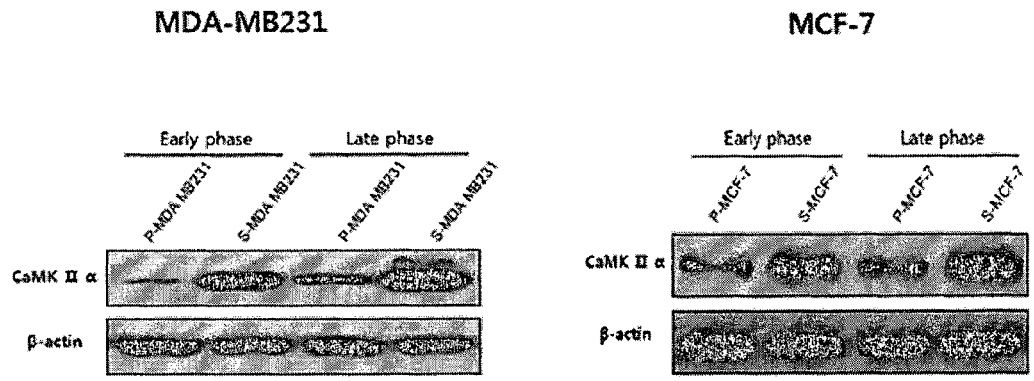
[FIG. 8]
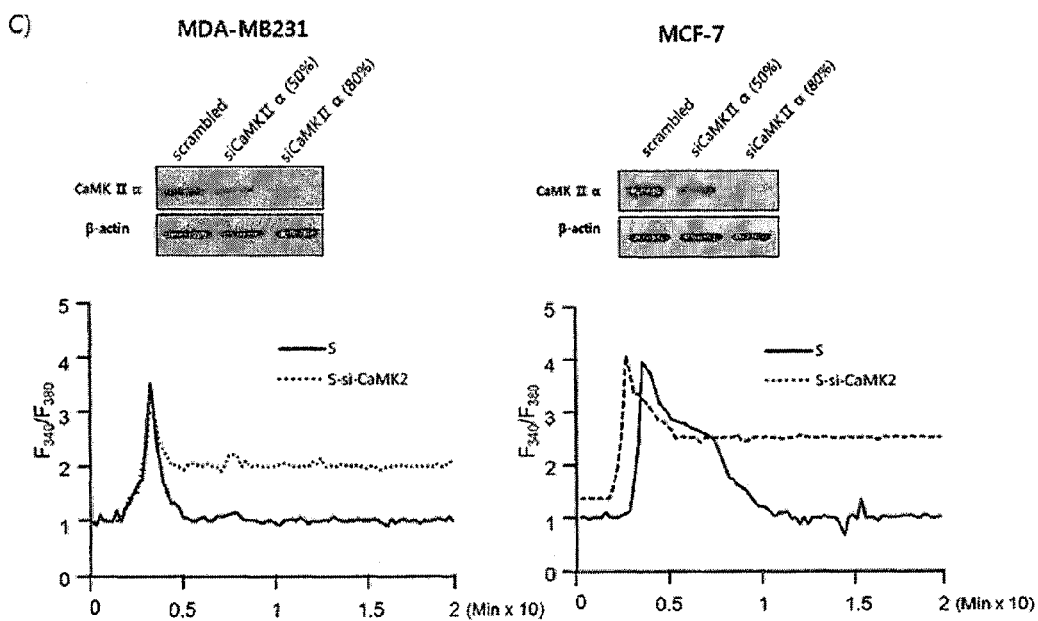

[FIG. 9]
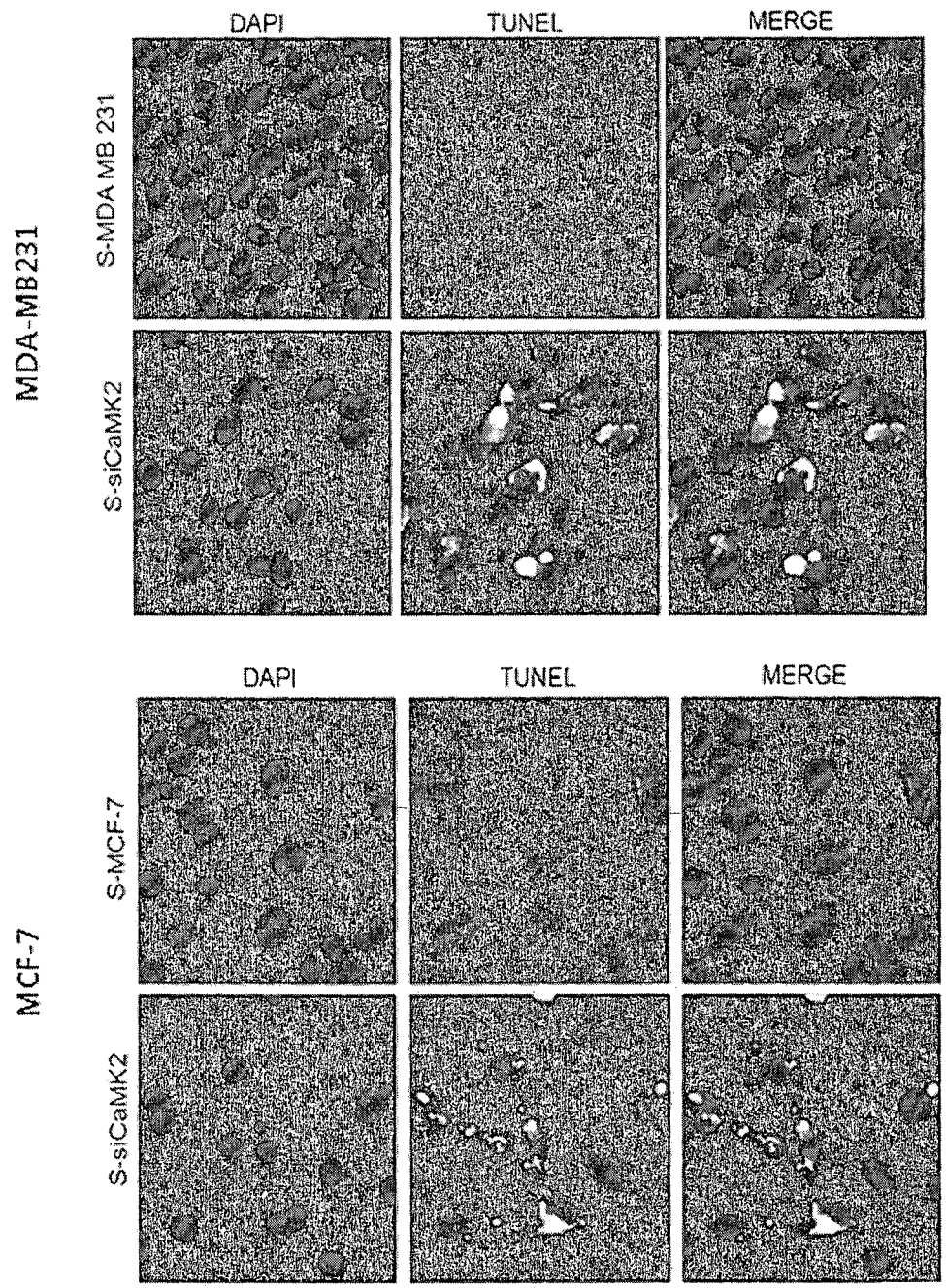

[FIG. 10]
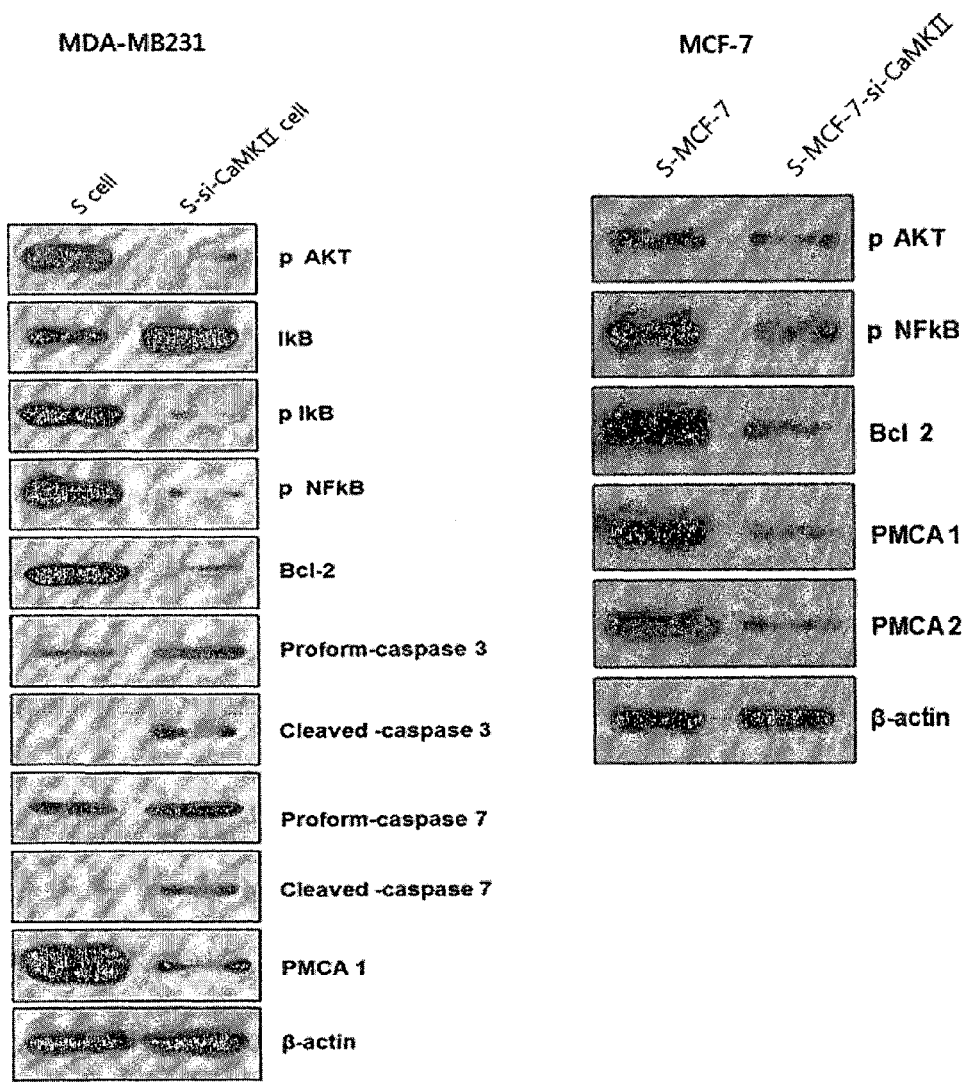

[FIG. 11]
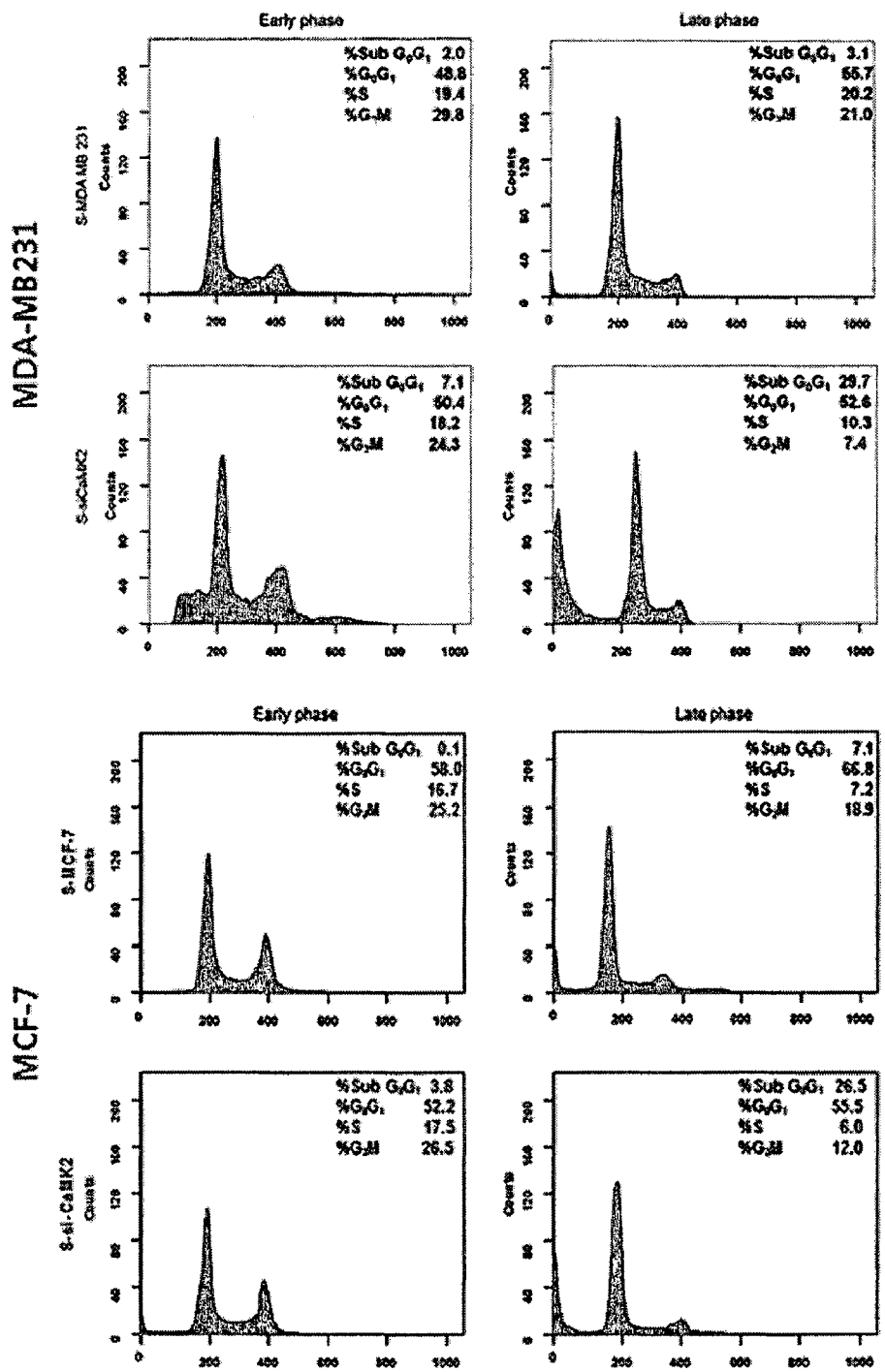

[FIG. 12]
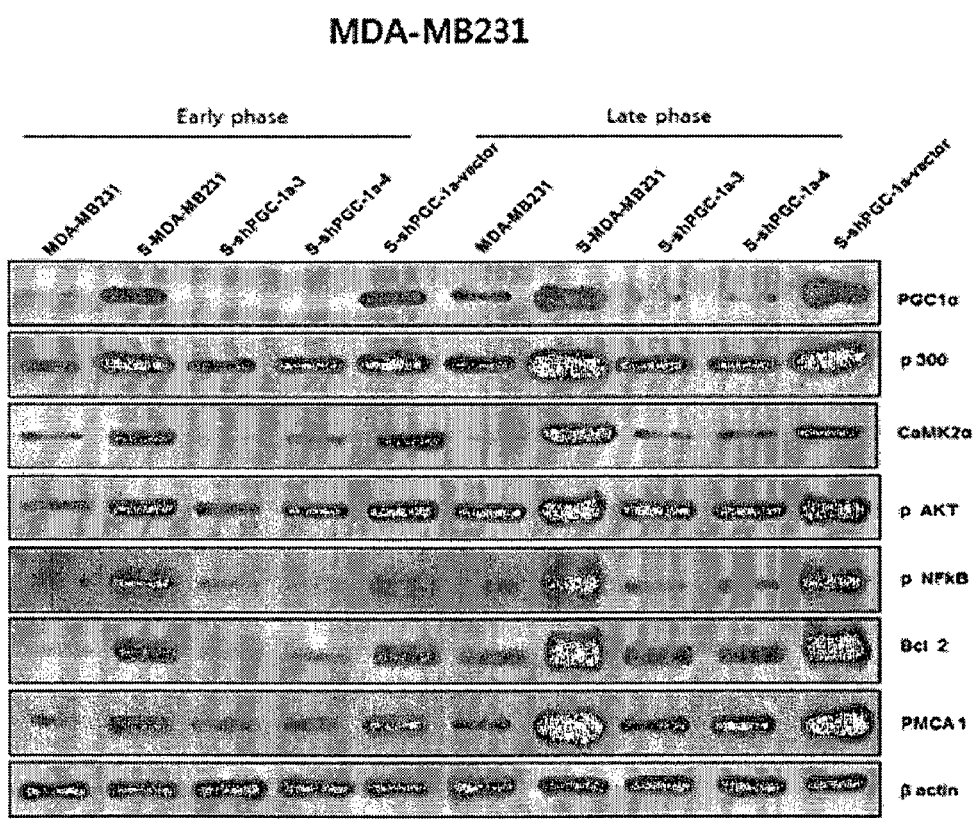

[FIG. 13]
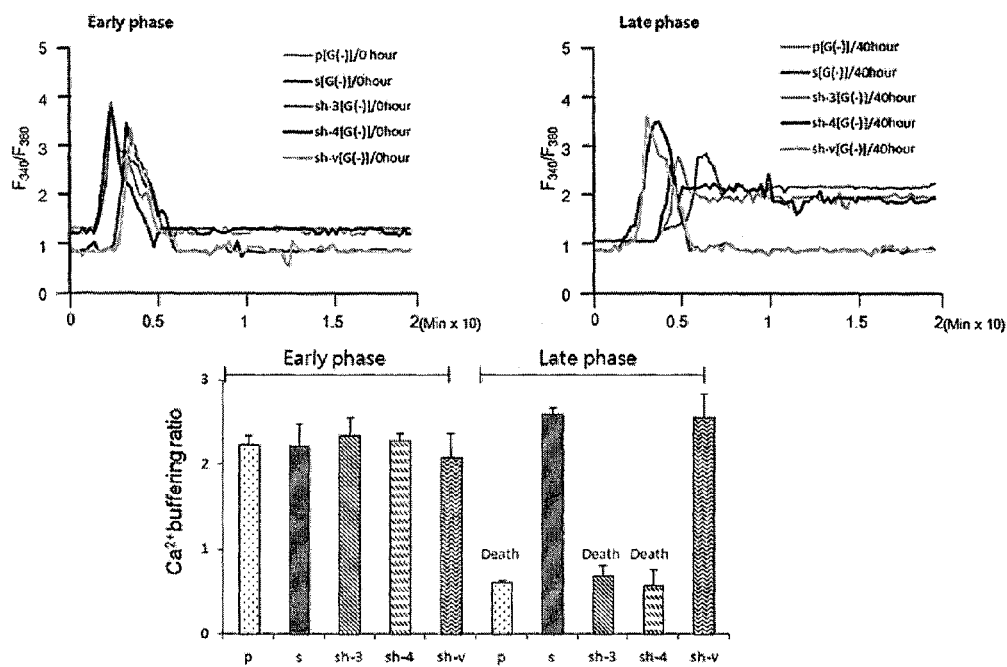

[FIG. 14]

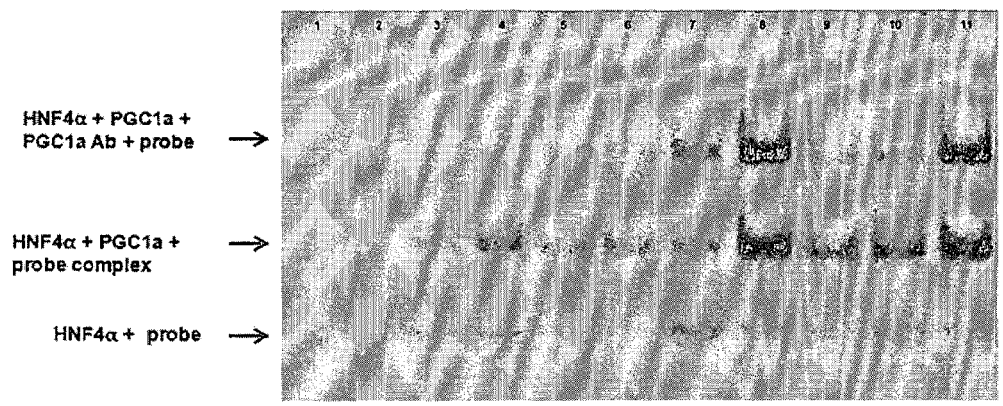

1. competitor(HNF4α hot probe + HNF4α cold probe) + nucleic extract
2. control(HNF4α hot probe, mutant) + nucleic extract
3. Ealry P (HNF4α hot probe + nucleic extract)
4. Ealry S (HNF4α hot probe + nucleic extract)

* 5~11: super shift.

5. Ealry P (HNF4α hot probe + nucleic extract) + anti-PGC1α 3ug
6. Ealry S (HNF4α hot probe + nucleic extract) + anti-PGC1α 3ug
7. Late P (HNF4α hot probe + nucleic extract) + anti-PGC1α 3ug
8. Late S (HNF4α hot probe + nucleic extract) + anti-PGC1α 3ug
9. Late sh-3 (HNF4α hot probe + nucleic extract) + anti-PGC1α 3ug
10. Late sh-4 (HNF4α hot probe + nucleic extract) + anti-PGC1α 3ug
11. Late sh-v (HNF4α hot probe + nucleic extract) + anti-PGC1α 3ug

[FIG. 15]

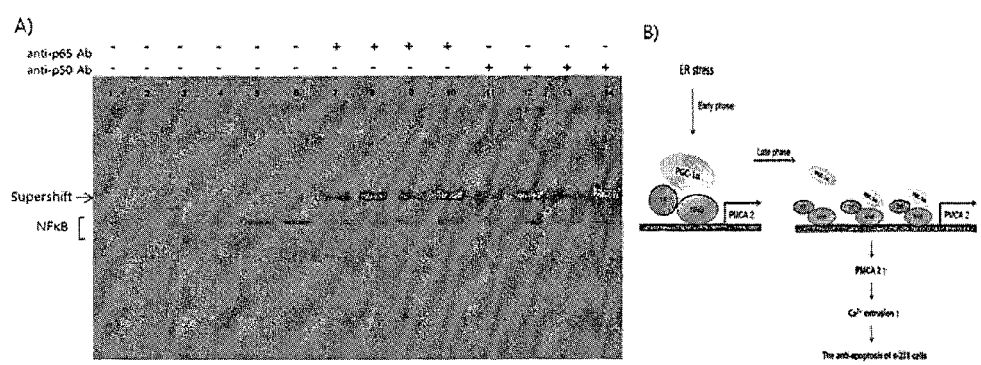

1. Competitor (NFkB hot probe + NFkB cold probe) + nucleic extract
2. Control (NFkB hot probe, mutant) + nucleic extract
3. Early P-MCF-7 (NFkB hot probe + nucleic extract)
4. Early S-MCF-7 (NFkB hot probe + nucleic extract)
5. Late P-MCF-7 (NFkB hot probe + nucleic extract)
6. Late S-MCF-7 (NFkB hot probe + nucleic extract)
7. Eady P-MCF-7 (NFkB hot probe + nucleic extract) + NFkB Ab$_{65}$
8. Early S-MCF-7 (NFkB hot probe + nucleic extract) + NFkB Ab$_{65}$
9. Late P-MCF-7 (NFkB hot probe + nucleic extract) + NFkB Ab$_{65}$
10. Late S-MCF-7 (NFkB hot probe + nucleic extract) + NFkB Ab$_{65}$
11. Early P-MCF-7 (NFkB hot probe + nucleic extract) + NFkB Ab$_{50}$
12. Early S-MCF-7 (NFkB hot probe + nucleic extract) + NFkB Ab$_{50}$
13. Late P-MCF-7 (NFkB hot probe + nucleic extract) + NFkB Ab$_{50}$
14. Late S-MCF-7 (NFkB hot probe + nucleic extract) + NFkB Ab$_{50}$

[FIG. 16]
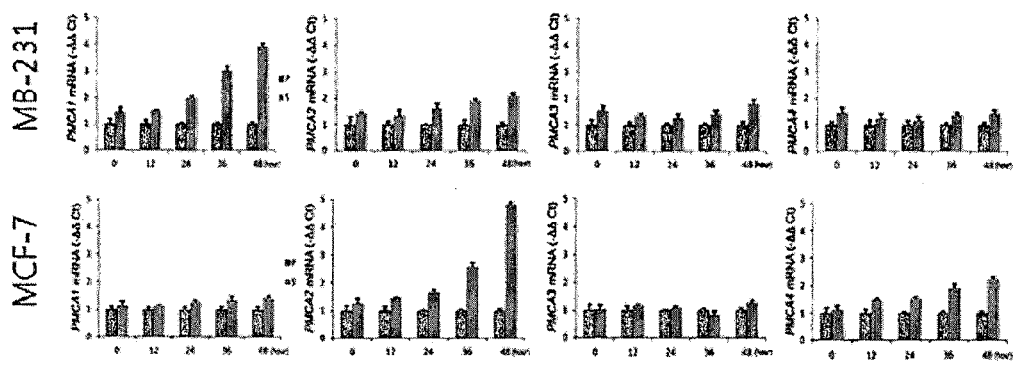
[FIG. 17]
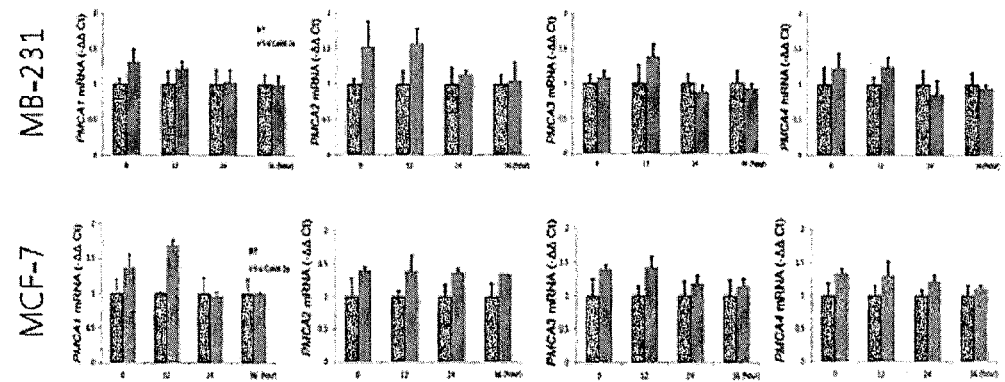

[FIG. 18]
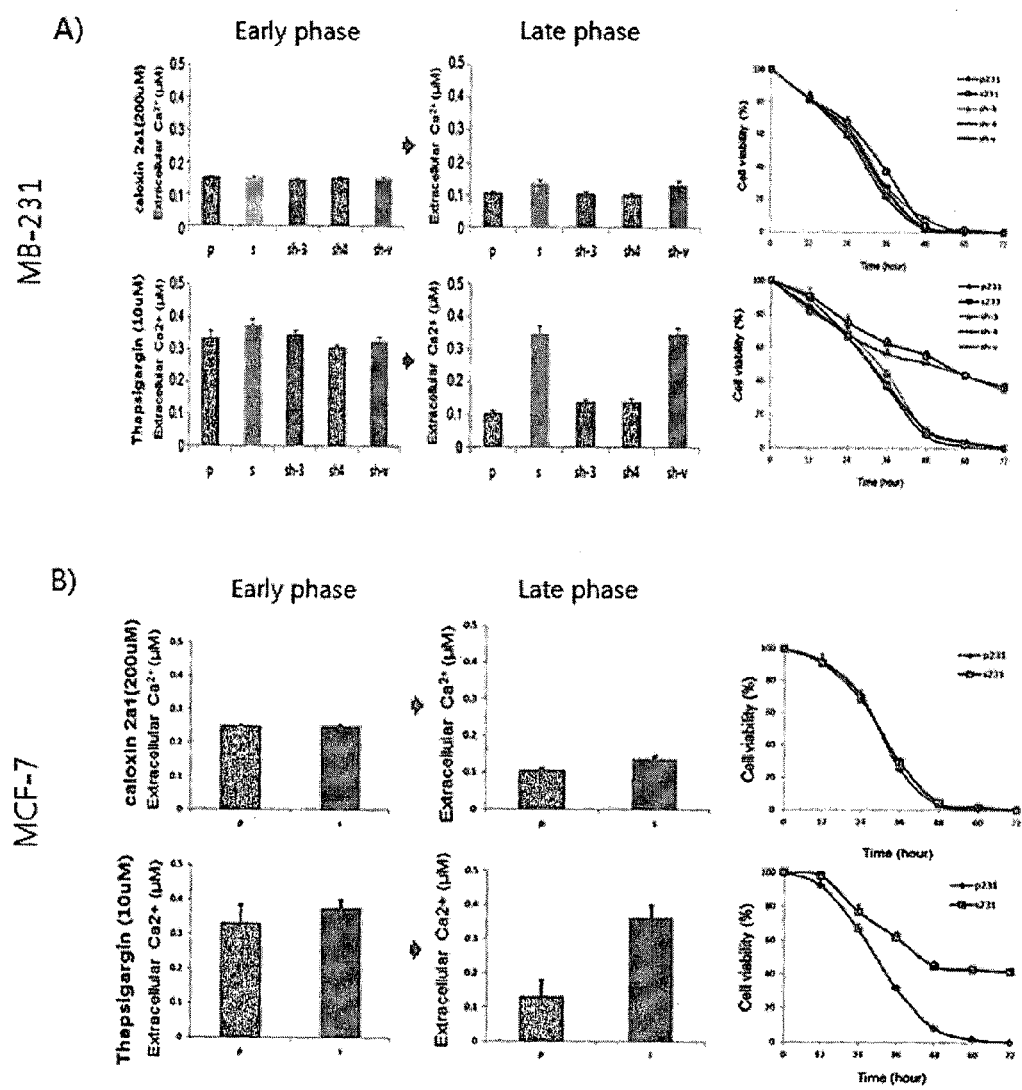

[FIG. 19]
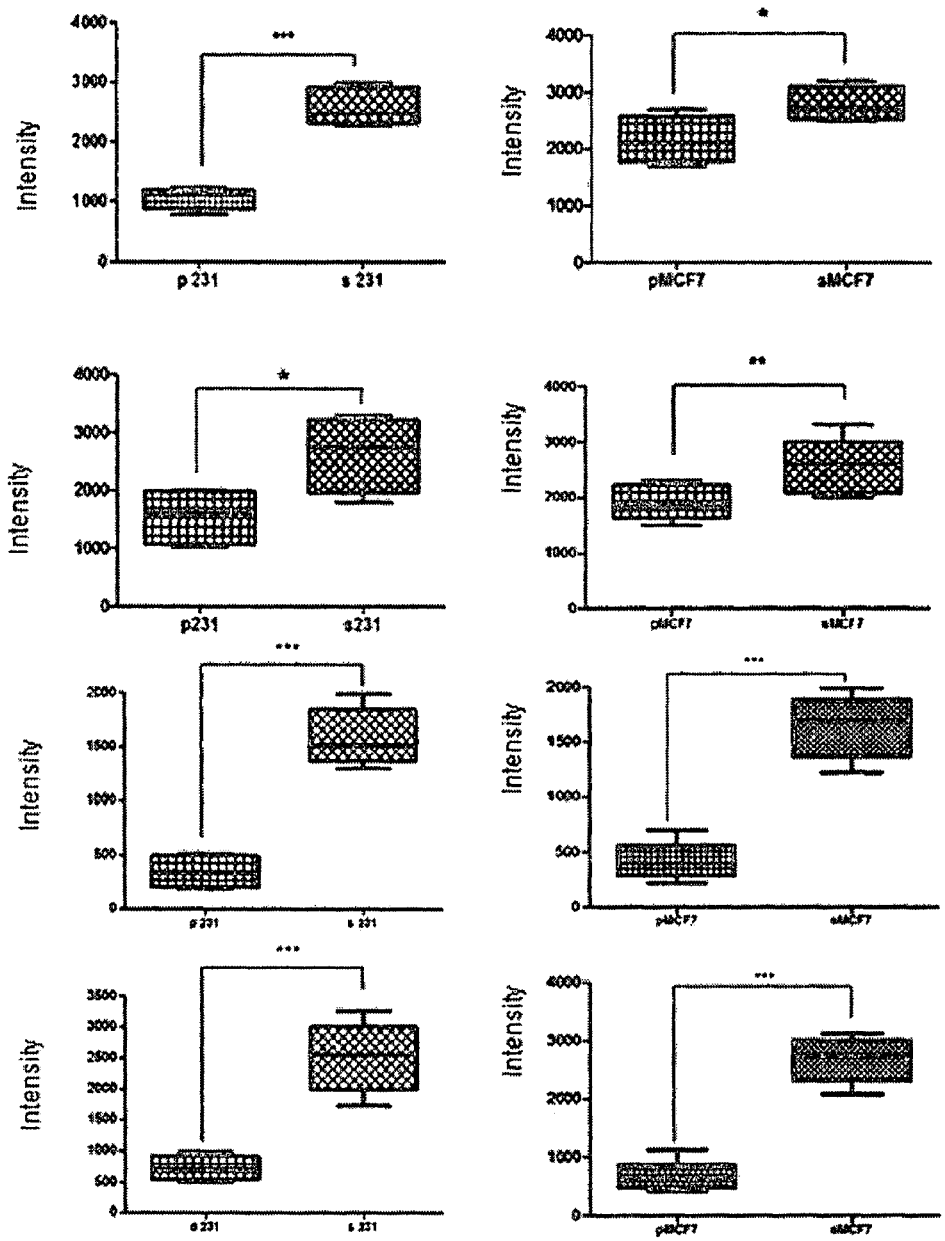

[FIG. 20]
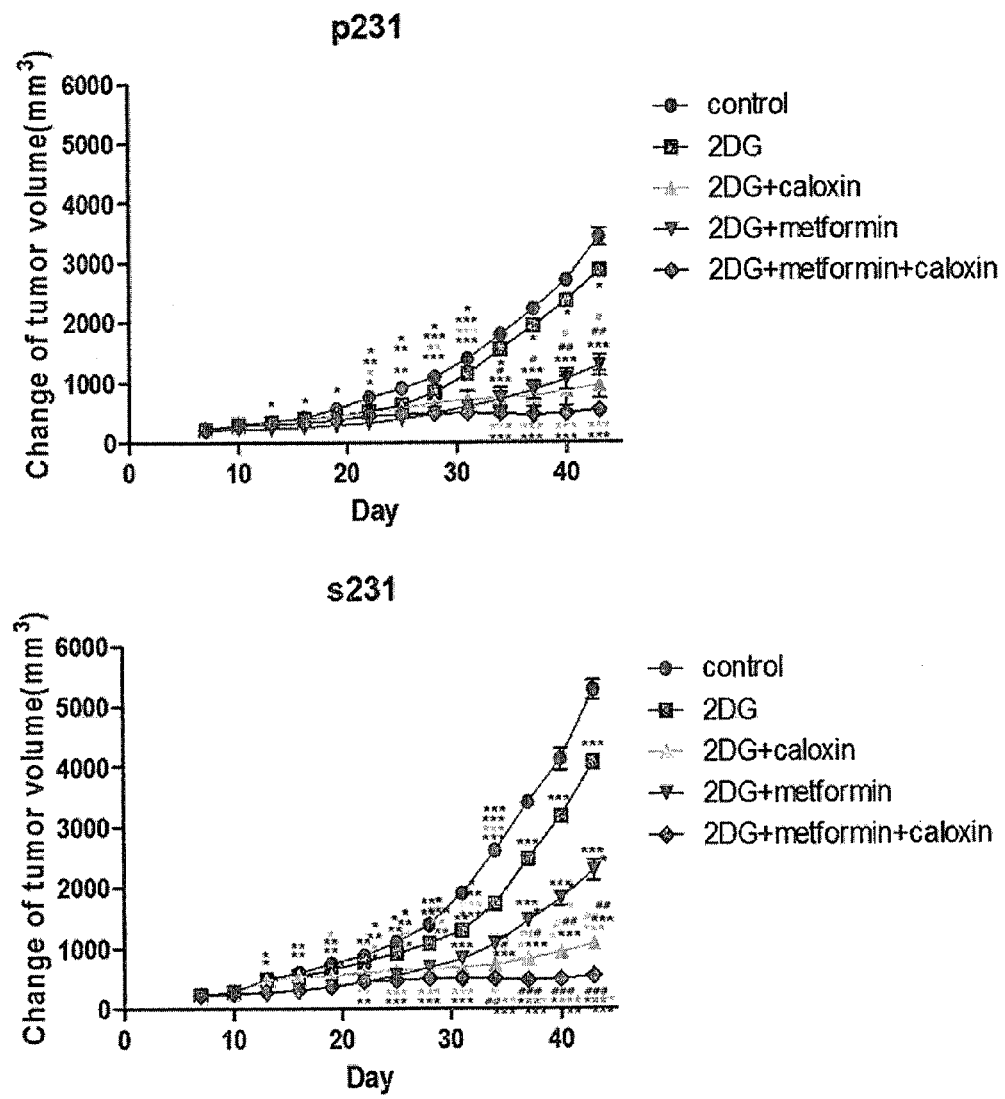

[FIG. 21]
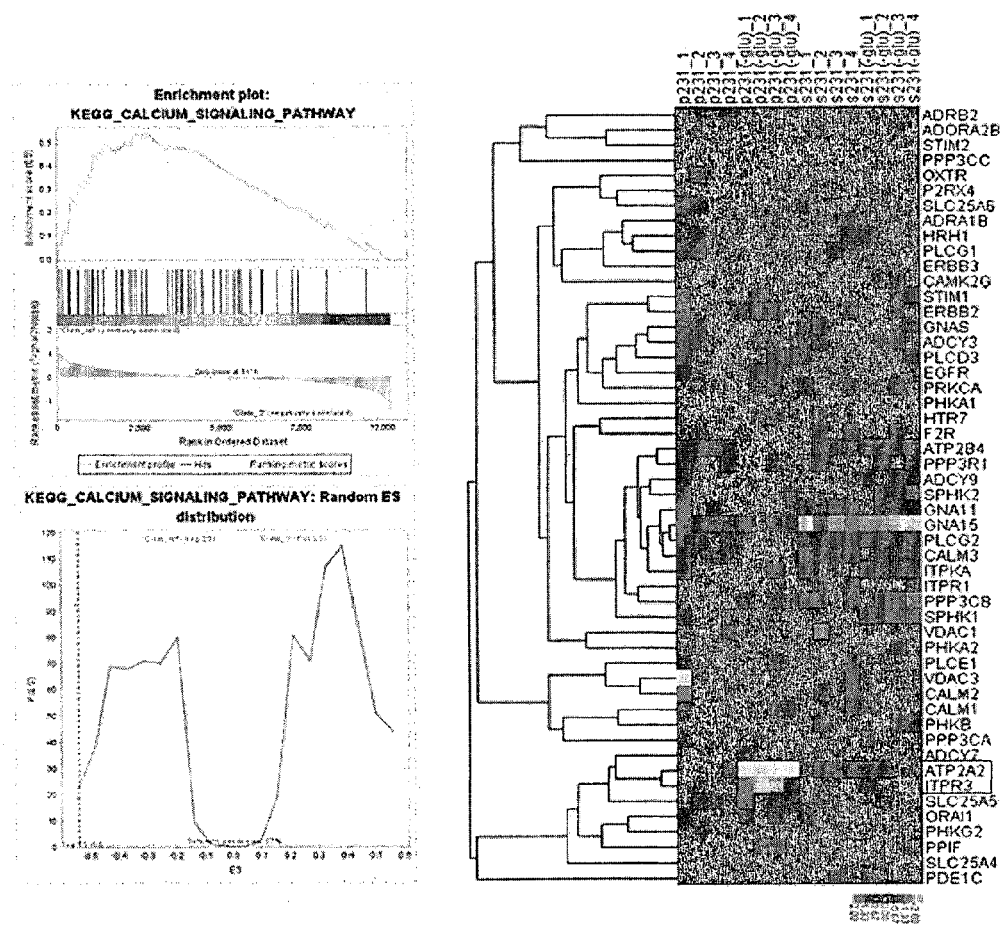

[FIG. 22]
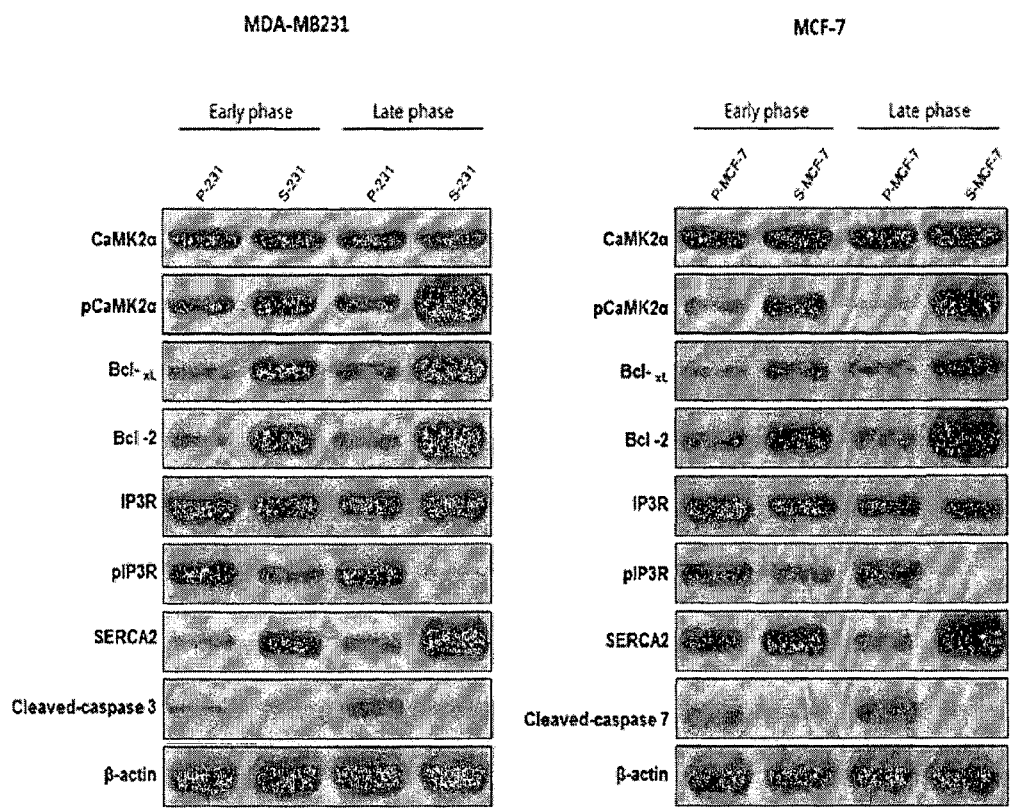

[FIG. 23]
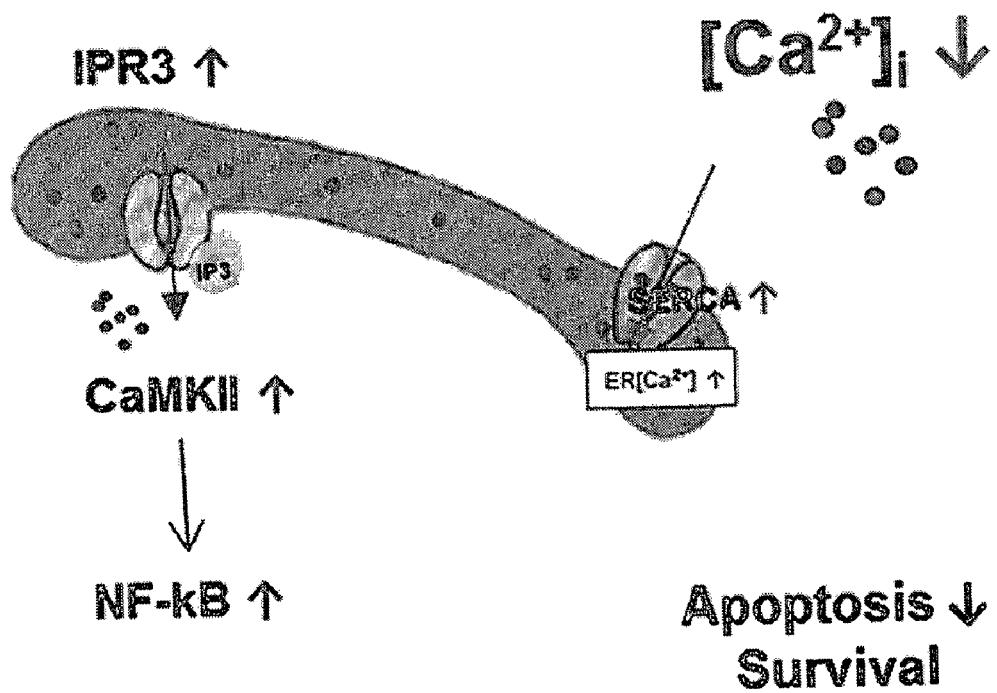

[FIG. 24]
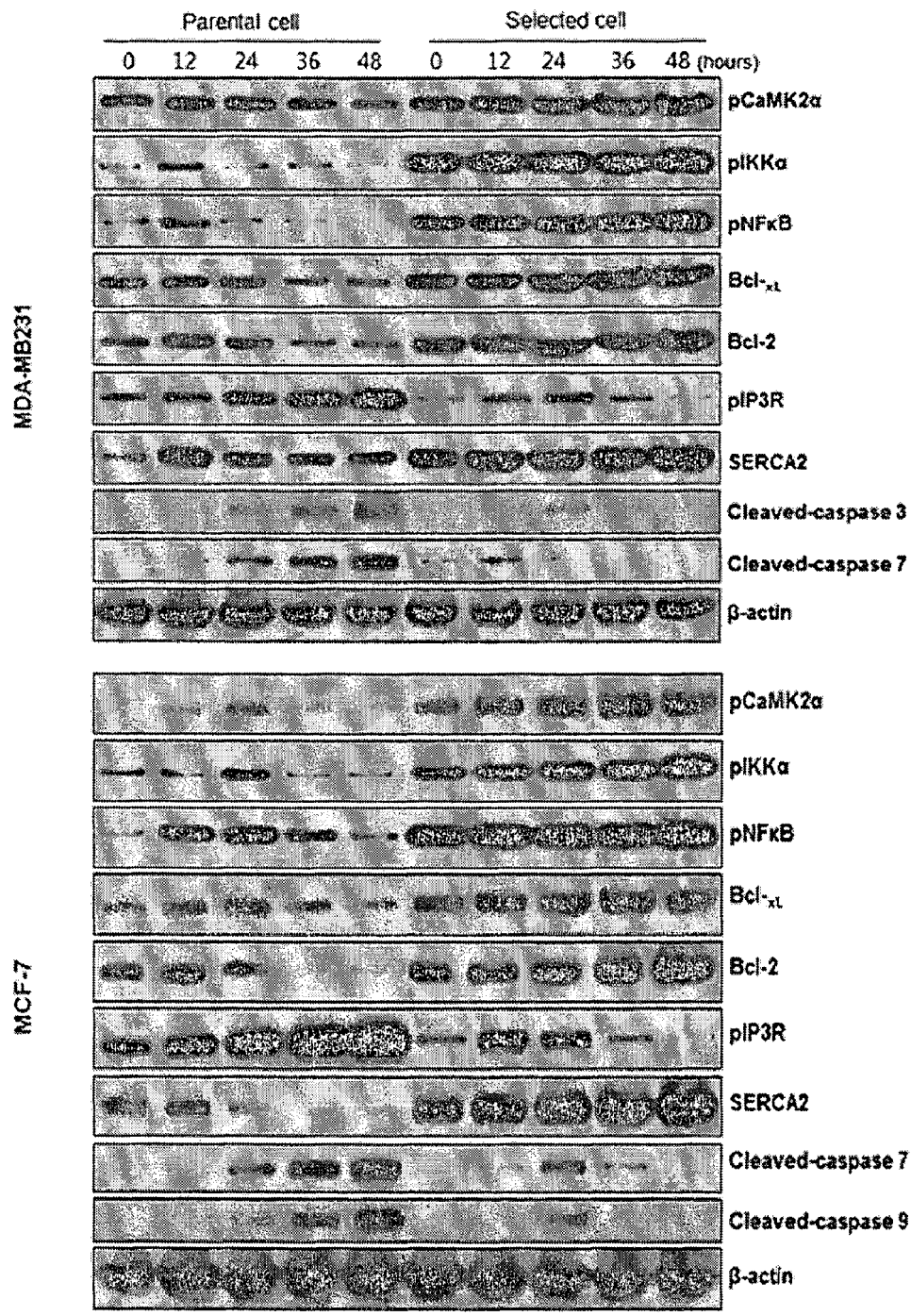

[FIG. 25]
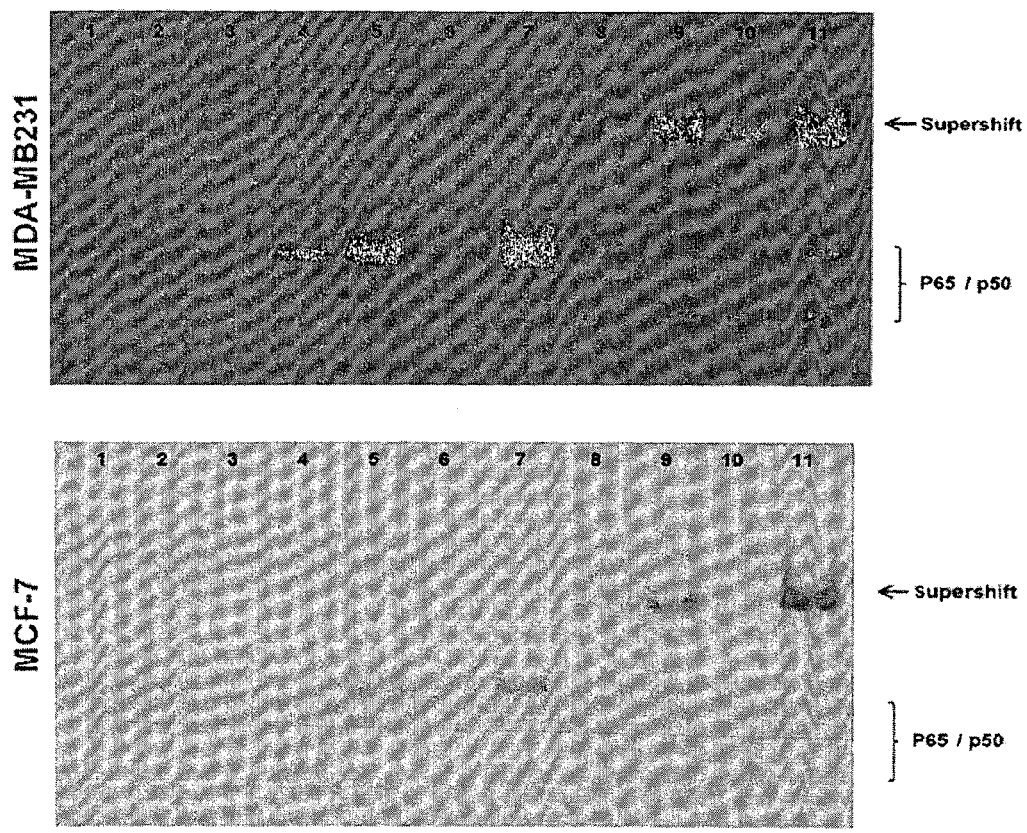

[FIG. 26]
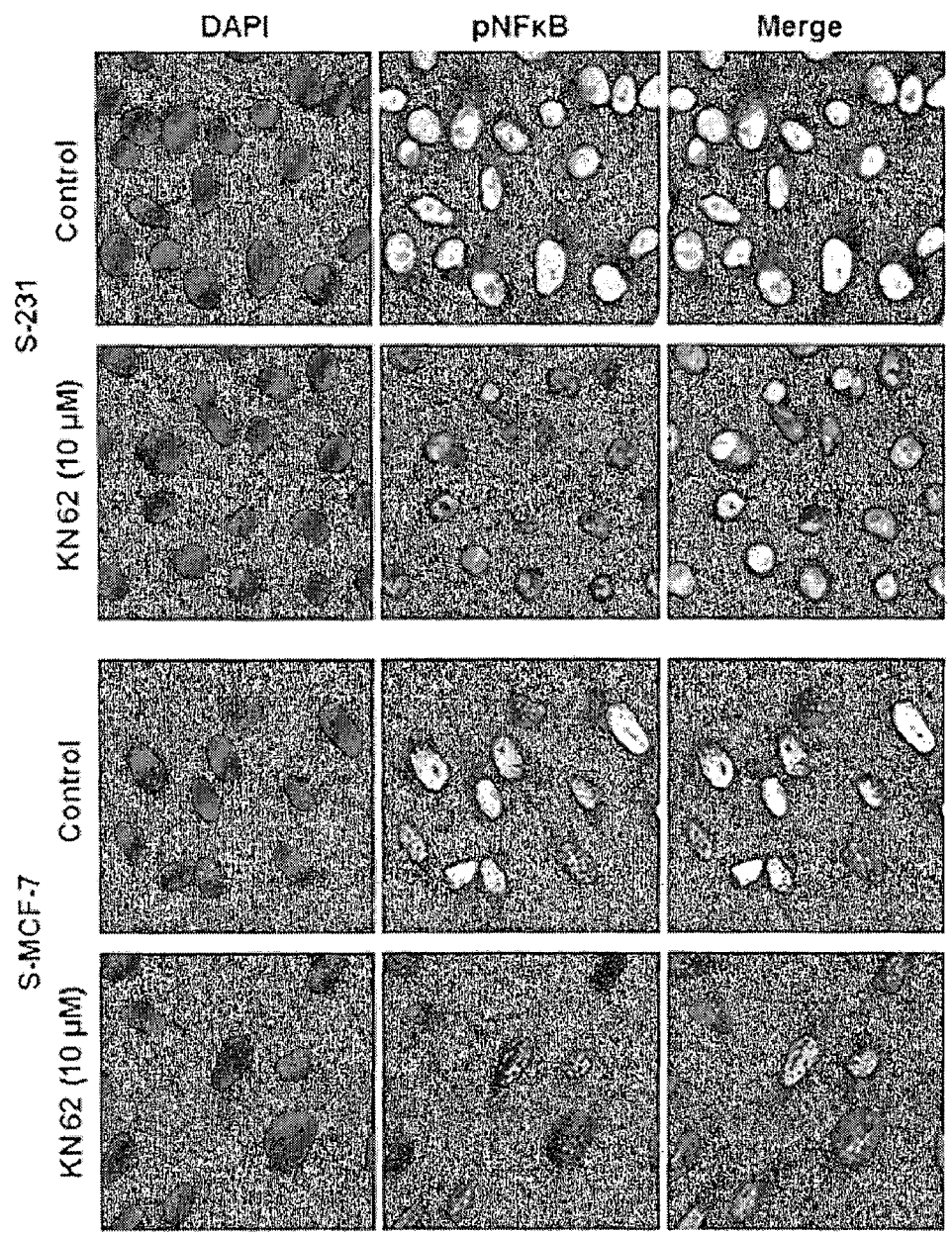

[FIG. 27]
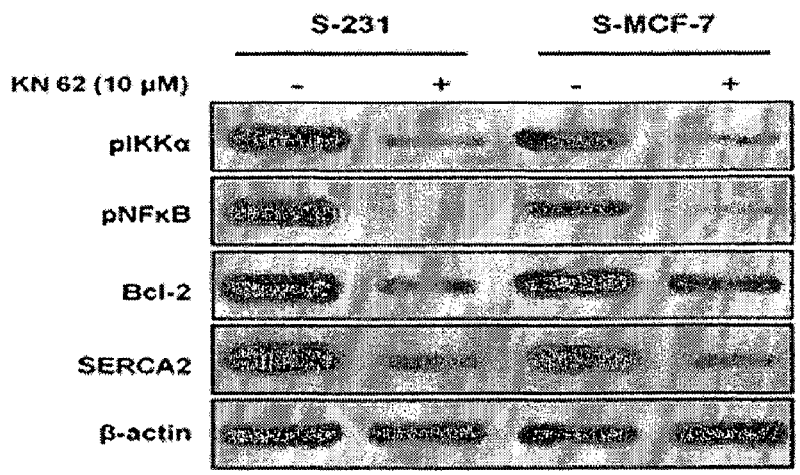
[FIG. 28]
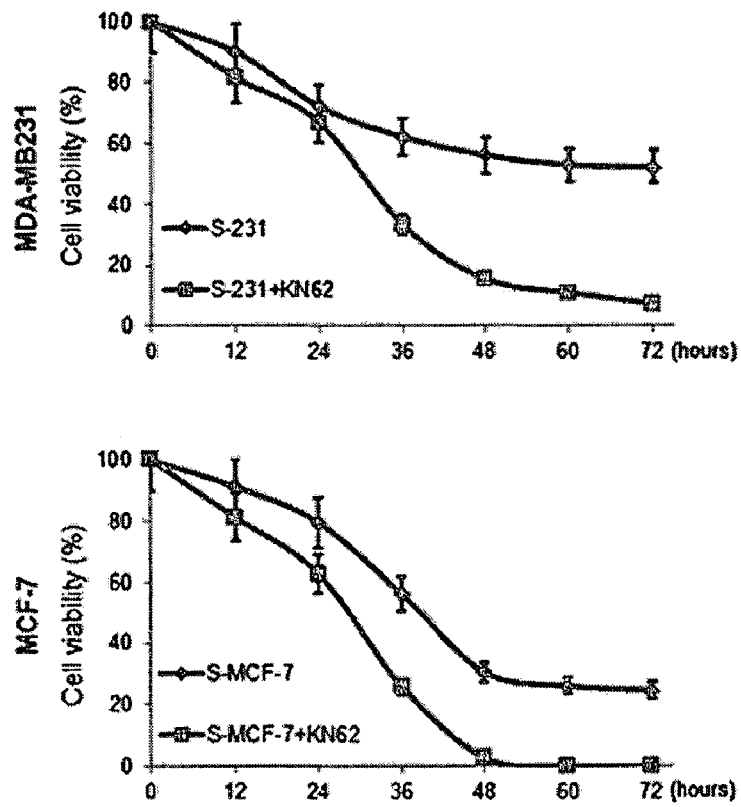

[FIG. 29]
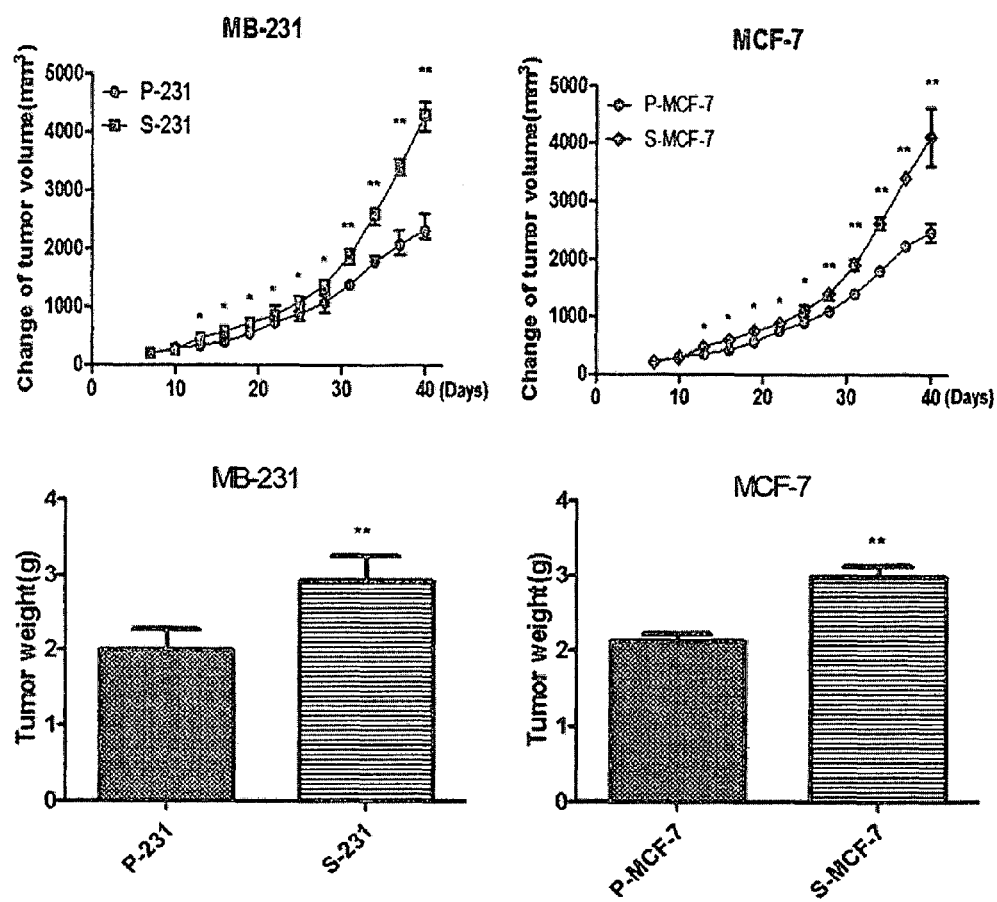

[FIG. 30]
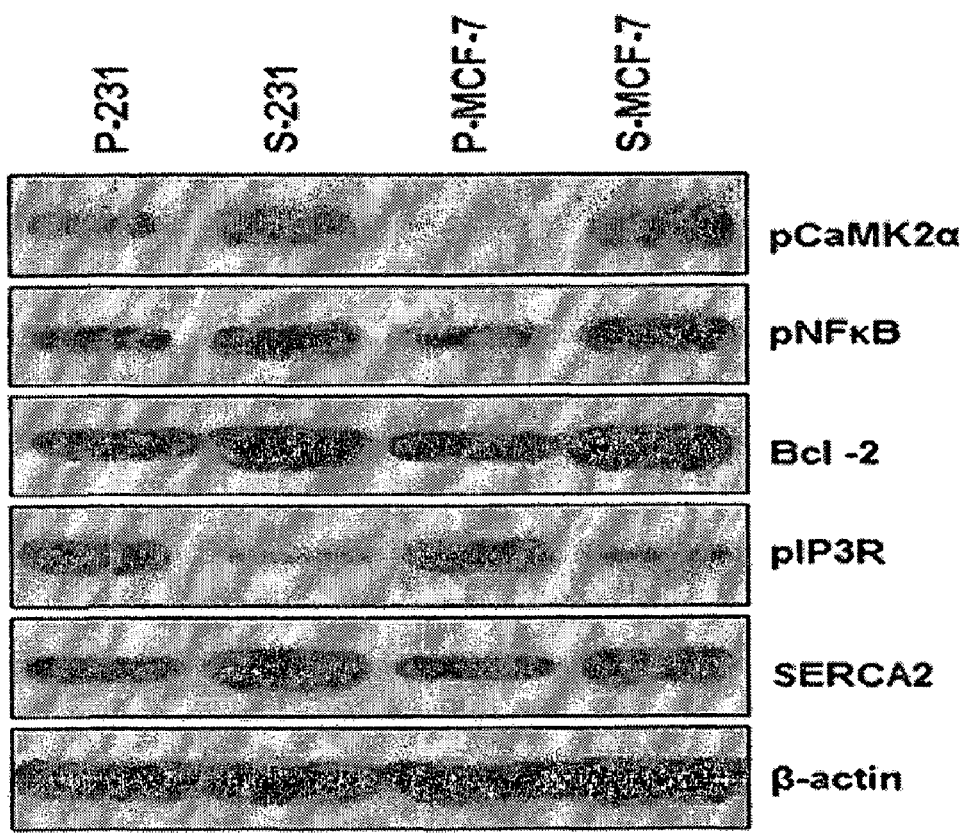

[FIG. 31]
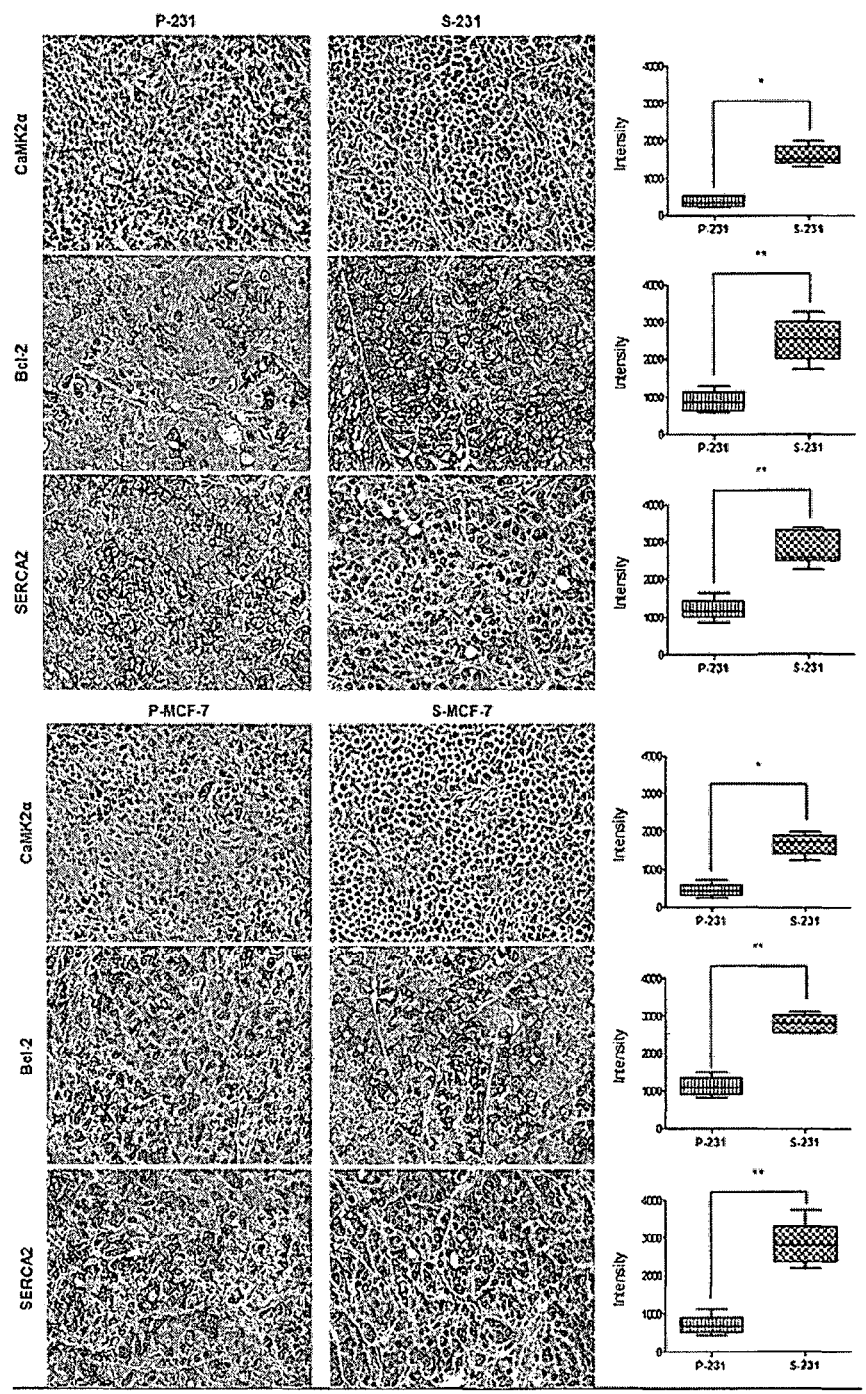

COMPOSITION FOR TREATING CANCER STEM CELLS

TECHNICAL FIELD

The present invention relates to a composition for treating cancer stem cells, which contains a glucose uptake inhibitor and a calcium pump inhibitor.

BACKGROUND ART

Anticancer drugs, which have recently been actively developed and are actually used in anticancer therapy, are mostly drugs targeting cancer cells that proliferate rapidly. In the case of anticancer therapy using such drugs, it appears that cancer cells are effectively killed in the initial stage, suggesting that cancer is treated. However, cancer stem cells remaining in the body are not removed, and thus cancer recurrence and/or metastasis actively occurs. Ultimately, problems often arise resistance to existing anticancer therapy appears. For this reason, cancer stem cells have recently been of increasing interest. It is known that cancer stem cells are cancer cells that have the ability to self-renew unlimitedly, like ordinary stem cells, and proliferate slowly, unlike ordinary cancer cells, and also have the ability to self-renew or differentiate, which is characteristic of stem cells. Furthermore, such cancer stem cells are known to have mechanisms different from those of previously known cancer cells. However, studies on cancer stem cells have not yet been actively conducted, and particularly, there are little or no studies on drugs for treating cancer stem cells, which target cancer stem cells (Korean Patent Application No. 10-2011-0066035).

Accordingly, it is expected that the development of a composition for treating cancer stem cells, which is effective against cancer stem cells, can provide an effective therapeutic method that can increase the cancer treatment effect and that can inhibit cancer recurrence and/or metastasis.

DISCLOSURE

Technical Problem

The present invention has been made in order to solve the above-described problems occurring in the prior art, and it is an object of the present invention to provide a composition for treating cancer stem cells, which contains a glucose uptake inhibitor and a calcium pump inhibitor.

However, the technical object to be achieved by the present invention is not limited to the above technical object, and other objects that are not mentioned above can be clearly understood by those skilled in the art from the following description.

Technical Solution

Hereinafter, various embodiments described herein will be described with reference to figures. In the following description, numerous specific details are set forth, such as specific configurations, compositions, and processes, etc., in order to provide a thorough understanding of the present invention. However, certain embodiments may be practiced without one or more of these specific details, or in combination with other known methods and configurations. In other instances, known processes and preparation techniques have not been described in particular detail in order to not unnecessarily obscure the present invention. Reference throughout this specification to "one embodiment" or "an embodiment" means that a particular feature, configuration, composition, or characteristic described in connection with the embodiment is included in at least one embodiment of the present invention. Thus, the appearances of the phrase "in one embodiment" or "an embodiment" in various places throughout this specification are not necessarily referring to the same embodiment of the present invention. Additionally, the particular features, configurations, compositions, or characteristics may be combined in any suitable manner in one or more embodiments.

As used herein, the term "cancer stem cells" refers comprehensively refer to cancer cells having the ability to self-renew or differentiate, which is characteristic of stem cells. The cancer stem cells can proliferate at a slow rate, unlike ordinary cancer cells, under a normal tumor growth condition (which refers to a situation where essential nutrients (glucose) for cell growth are sufficient and tumor microenvironment conditions are abundant so that there is no cell stress), or can be kept in a dormant state, and thus can have resistance to anticancer drugs. For example, in the cancer stem cells, expression of transcriptional regulators such as PGC-1α can be regulated, unlike that in ordinary tumor cells, and thus the function of major metabolic regulators can differ from that in ordinary cancer cells. Through this different metabolic regulatory ability and the regulation of signaling systems mechanistically connected thereto, the cancer stem cells acquire resistance to apoptosis under nutrient deprivation and have the ability to invade and/or metastasize. However, the cancer stem cells are not limited thereto, as long as they can differentiate into ordinary cancer cells.

The present invention provides a pharmaceutical composition for inhibiting cancer stem cell growth or treating cancer stem cells, which contains, as active ingredients, a glucose uptake inhibitor and a calcium pump inhibitor.

In one embodiment of the present invention, the glucose uptake inhibitor is preferably a glucose derivative, and more preferably 2-deoxyglucose (2DG), but it is not limited thereto, as long as it is a compound that inhibits the uptake of glucose (that is an energy source for cells) to induce nutrient deprivation and/or metabolic energy exhaustion-associated endoplasmic reticulum stress to thereby inhibit cell growth and induce expression of plasma membrane $Ca^{2+}$ ATPase (PMCA) in cancer stem cells. As used herein, the term "glucose derivative" means a compound which is obtained by modifying a portion of glucose and which acts competitively with normal glucose to inhibit glucose uptake.

In another embodiment of the present invention, the calcium pump inhibitor is preferably an inhibitor of plasma membrane $Ca^{2+}$ ATPase (PMCA), an inhibitor of $Ca^{2+}$/calmodulin-dependent kinase-2-alpha (CaMK-2α), or the like. More preferably, the calcium pump inhibitor may be caloxin, nifedipine, KN62 (1-[N,O-bis(5-isoquinolinesulphonyl)-N-methyl-L-tyrosyl]-4-phenylpiperazine), an siRNA that binds specifically to CaMK-2α, or the like, but it is not limited thereto as long as it is a substance capable of inhibiting the ability of cancer stem cells to control intracellular calcium concentration. As used herein, the term "inhibitor of PMCA" refers to a substance capable of inhibiting the activity of PMCA to inhibit extracellular release of calcium.

In still another embodiment of the present invention, the composition may further contain a biguanide-based compound. The biguanide-based compound is preferably a biguanide-based drug for treating diabetes. More preferably, the biguanide-based compound may be metformin, phenformin, buformine, or the like, but it is not limited thereto, as long as it is a biguanide-based compound that interferes with intracellular energy production to induce a nutrient deficiency-like state.

In still another embodiment of the present invention, the cancer may preferably be breast cancer, uterine cancer, gastric cancer, brain cancer, rectal cancer, colorectal cancer, lung cancer, skin cancer, ovarian cancer, renal cancer, blood cancer, pancreatic cancer, prostate cancer, thyroid cancer, liver cancer or the like. More preferably, the cancer may be breast cancer, but it is not limited thereto as long as it is cancer whose progression (such as tumor differentiation and/or growth) is dependent on cancer stem cells described in the present invention.

The pharmaceutical composition for treating cancer stem cells may also be administered in combination with other anticancer drugs in order to effectively treat not only cancer stem cells, but also ordinary cancer cells. In addition, the pharmaceutical composition may also be used as a pharmaceutical composition for inhibiting cancer recurrence or metastasis.

In the present invention, the pharmaceutical composition may be in the form of capsule, tablet, granule, injectable solution, ointment, powder or beverage, and may be administered to a human subject. For use, the pharmaceutical composition may be prepared as oral formulations, including powders, granules, capsules, tablets, aqueous suspensions and the like, suppositories for external use, and sterile injectable solutions, according to conventional methods respectively, but is not limited thereto. The pharmaceutical composition of the present invention may contain a pharmaceutically acceptable carrier. For oral administration, the pharmaceutically acceptable carrier may include one or more of binders, lubricants, disintegrants, excipients, solubilizing agents, dispersing agents, stabilizers, suspending agents, pigments, fragrances, and the like. For injection, the pharmaceutically acceptable carrier may include one or more of buffers, preservatives, pain-relieving agents, solubilizing agents, isotonic agents, stabilizers, and the like. For local administration, the pharmaceutically acceptable carrier may include one or more of bases, excipients, lubricants, preservatives, and the like. The pharmaceutical composition according to the present invention may be mixed with the pharmaceutically acceptable carriers as described above to provide various formulations. For example, for oral administration, the pharmaceutical composition of the present invention may be prepared in the form of tablet, troche, capsule, elixir, suspension, syrup, wafer or the like, and for injection, the pharmaceutical composition may be prepared in the form of unit dosage ampoules or multiple dosage containers. In addition, the pharmaceutical composition of the present invention may be prepared as solutions, suspensions, tablets, capsules, sustained-release formulations, or the like.

Meanwhile, examples of carriers, excipients and diluents, which are suitable for formulation, include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil, or the like. In addition, the pharmaceutical composition of the present invention may further contain one or more of fillers, anticoagulants, lubricants, wetting agents, fragrances, emulsifiers, preservatives, and the like.

Routes for administration of the pharmaceutical composition according to the present invention include, but are not limited to, oral, intravenous, intramuscular, intra-arterial, intra-marrow, intrathecal, intracardiac, transdermal, subcutaneous, intraperitoneal, intranasal, intestinal intrarectal, local, sublingual and intrarectal routes. Oral or parenteral administration is preferred. As used herein, the term "parenteral" is meant to include subcutaneous, intradermal, intravenous, intramuscular, intra-articular, intrabursal, intestinal, intrathecal, intralesional and intracranial injection or infusion techniques. The pharmaceutical composition of the present invention may also be administered in the form of suppositories for rectal administration.

The dose of the pharmaceutical composition of the present invention may vary depending on the activity of a particular compound used, the patient's age, body weight, general health, sex, diet, administration time, the route of administration, excretion rate, drug combination, and the severity of a particular disease to be prevented or treated. The pharmaceutical composition may be administered at a dose of 0.0001-50 mg/kg/day or 0.001-50 mg/kg/day, depending on the patient's condition, body weight, the severity of the disease, the form of drug, the route of administration, and the period of administration. The pharmaceutical composition of the present invention may be administered once or several times a day. The dose does not limit the scope of the present invention in any way. The pharmaceutical composition according to the present invention may be formulated as pills, sugar-coated tablets, capsules, liquids, gels, syrups, slurries, or suspensions.

Advantageous Effects

The composition for treating cancer stem cells according to the present invention contains a glucose uptake inhibitor and a calcium pump inhibitor. The composition of the present invention contains the glucose uptake inhibitor and a biguanide-based drug, which induce nutrient deprivation and a metabolic energy exhaustion-associated endoplasmic reticulum stress to thereby induce expression of plasma membrane $Ca^{2+}$ ATPase (PMCA) in cancer stem cells. Furthermore, the composition of the present invention also contains the calcium pump inhibitor which can reduce the resistance of cancer stem cells to $Ca^{2+}$-associated apoptosis to thereby induce cancer stem cell death, suggesting that the composition may be used as an effective agent for treating cancer stem cells. Accordingly, it is expected that the composition of the present invention can effectively treat various cancer stem cells to thereby inhibit cancer recurrence and/or metastasis.

DESCRIPTION OF DRAWINGS

FIG. 1 shows the results of determining the viabilities of s-MDA-MB-231 and s-MCF-7 cell lines under glucose deprivation by crystal violet staining according to an example of the present invention.

FIG. 2 shows the results of determining the viabilities of s-MDA-MB-231 and s-MCF-7 cell lines under glucose deprivation by a MTT assay according to an example of the present invention.

FIG. 3 shows the results of a TUNEL assay performed according to an example of the present invention.

FIG. 4 shows the results of immunoblot analysis performed according to an example of the present invention.

FIG. 5 shows the results of cell cycle analysis performed according to an example of the present invention.

FIG. 6 shows the results of analyzing the level of intracellular $Ca^{2+}$ according to an example of the present invention.

FIG. 7 shows the results of analyzing the expression level of CaMK-2α according to an example of the present invention.

FIG. 8 shows the results of analyzing the levels of intracellular $Ca^{2+}$ in cell lines, in which expression of CaMK-2α was inhibited, according to an example of the present invention.

FIG. 9 shows the results of a TUNEL assay on cell lines in which expression of CaMK-2α was inhibited, according to an example of the present invention.

FIG. 10 shows the results of immunoblot analysis of cell lines in which expression of CaMK-2α was inhibited, according to an example of the present invention.

FIG. 11 shows the results of cell cycle analysis of cell lines in which expression of CaMK-2α was inhibited, according to an example of the present invention.

FIG. 12 shows the results of analyzing the relationship between PGC-1α and CaMK-2α according to an example of the present invention.

FIG. 13 shows the results of determining the levels of intracellular $Ca^{2+}$ in cell lines, in which expression of PGC-1α was inhibited, according to an example of the present invention.

FIG. 14 shows the results of analyzing the binding relationship between PGC-1α and PMCA1 by EMSA according to an example of the present invention.

FIG. 15 shows the results of analyzing the binding relationship between PGC-1α and PMCA2 by EMSA according to an example of the present invention.

FIG. 16 shows the results of analyzing the expression level of PMCA under nutrient deprivation according to an example of the present invention.

FIG. 17 shows the results of analyzing the expression level of PMCA in cell lines, in which expression of CaMK-2α was inhibited, according to an example of the present invention.

FIG. 18 shows the results of analyzing the effect of a calcium pump inhibitor according to an example of the present invention.

FIG. 19 shows the results of analyzing protein expression in breast cancer animal models by immunochemical staining according to an example of the present invention.

FIG. 20 shows the results of analyzing the effect of co-administration to breast cancer animal models by immunochemical staining according to an example of the present invention.

FIG. 21 shows the results of analyzing the difference in gene expression between cancer cells and cancer stem cells according to an example of the present invention.

FIG. 22 shows the results of Western blot analysis of the expression of calcium regulation-related proteins in cancer cells and cancer stem cells according to an example of the present invention.

FIG. 23 is a schematic view schematically showing the calcium ion regulatory mechanism of cancer stem cells according to an example of the present invention.

FIG. 24 shows the time-dependent changes in CaMK-2α signaling mechanisms, measured according to an example of the present invention.

FIG. 25 shows the results of analyzing the role of pNF-kB according to an example of the present invention.

FIG. 26 shows the results of a TUNEL assay performed according to an example of the present invention.

FIG. 27 shows the results of Western blot analysis performed according to an example of the present invention.

FIG. 28 shows the results of determining cell viability according to an example of the present invention.

FIG. 29 shows the results of examining tumor growth in cancer stem cell-based animal models according to an example of the present invention.

FIG. 30 shows the results of analyzing protein expression levels in cancer stem cell-based animal models according to an example of the present invention.

FIG. 31 shows the results of analyzing protein expression levels in cancer stem cell-based animal models according to an example of the present invention.

BEST MODE

Hereinafter, the present invention will be described in further detail. It will be obvious to those skilled in the art that these examples are for illustrative purposes only and are not intended to limit the scope of the present invention.

EXAMPLE 1

Production of Cancer Stem Cells

In order to produce cancer stem cells, the long-term nutrient deprivation of p-MDA-MB-231 and p-MCF-7, which are the parental cells of MDA-MB-231 and MCF-7 cell lines (breast cancer cell lines), respectively, was induced, and survived cells (s-MDA-MB-231 and s-MCF-7) which avoided apoptosis under nutrient deprivation were selected and verified by analysis of biological characteristics specific for ordinary cancer stem cells, thereby producing cancer stem cells. In order to identify the mechanism of cancer stem cells and develop a therapeutic agent capable of inhibiting cancer stem cells, a shPGC-1αpGFP-V-RS vector (Origene) was transfected into each of the s-MDA-MB-231 and s-MCF-7 cell lines to thereby produce sshPGC-1α-MDA-MB-231 and s-shPGC-1α-MCF-7, which are stem cells that stably express shPGC-1α. The produced cell lines were used in the experiment. Each of the cell lines was cultured in RPMI-1640 medium containing 10% fetal bovine serum (FBS).

EXAMPLE 2

Determination of Viability of Cancer Stem Cells under Glucose Deprivation

In order to compare the viabilities of cancer cells and cancer stem cells under glucose deprivation, each of p-MDA-MB-231, p-MCF-7, s-MDA-MB-231 and s-MCF-7 cell lines, prepared in the same manner as described in Example 1, was added to a 96-well plate at a concentration of $5 \times 10^3$ cells/100 μL and cultured to a confluence of about 70%, and then the medium was replaced with a glucose-deprived in RPMI-1640 medium containing 10% FBS, and the cells were further cultured for 3 days. At each of 0, 12, 24, 36, 48, 60 and 72 hours, the viability of each of the cell lines was determined by crystal violet staining and an MTT (3-(4,5-dimethylthiazol-2-yl)-2,5-diphenyltetrazolium bromide) assay. The results of the crystal violet staining are shown in FIG. 1, and the results of the MTT assay are shown in FIG. 2.

As shown in FIG. 1, the cells attached to the surface of the culture plate was counted by crystal violet staining, and as a result, it was shown that the cancer stem cell lines (s-MDA-MB-231 and s-MCF-7) showed significantly high viabilities compared to the parental cell lines (p-MDA-MB-231 and p-MCF-7).

Furthermore, as shown in FIG. 2, in the early phase of culture (after 12 hours of culture), there was no significant difference in cell viability between the cancer stem cells and the ordinary cancer cells; however, as it went toward the late phase of culture (after 48 hours of culture), there was a significant difference in cell viability between the cancer stem cells and the ordinary cancer cells. Particularly, in the case of the s-MDA-MB231 cell line, it was shown that the difference in cell viability between the cancer cells and the cancer stem cells was 40% or more.

Through the above results, it was found that the cancer stem cells showed high viability compared to the ordinary cancer cells under glucose deprivation (i.e., nutrient deprivation), suggesting that the cancer stem cells have high resistance to nutrient deprivation (i.e., energy deprivation).

EXAMPLE 3

Analysis of Apoptotic Resistance Cancer Stem Cells 3.1: TUNEL Assay

In order to examine whether the reason why cancer stem cells show high viability under nutrient deprivation is because of their resistance to apoptosis, each of p-MDA-MB-231, p-MCF-7, s-MDA-MB-231 and s-MCF-7 cell lines, cultured under glucose deprivation for 40 hours in the same manner as described in Example 2, was collected and subjected to a TUNEL assay. In the TUNEL assay, the collected cells were fixed with 4% paraformaldehyde solution for 48 hours, and then stained using a Terminal Deoxynucleotidyl Transferase dUTP Nick end Labeling (TUNEL) kit according to the manufacturer's protocol, and the fluorescence images of the cells were acquired with a fluorescence microscope and analyzed using Zeiss LSM Image Browser software program. The results are shown in FIG. 3.

As shown in FIG. 3, in the ordinary cancer cell lines (p-MDA-MB-231 and p-MCF-7), DNA fragmentation caused by apoptosis was observed in a large number of cells; however, in the cancer stem cell lines (s-MDA-MB-231 and s-MCF-7), DNA fragmentation was observed in a smaller number of cells. This suggests that the cancer stem cells had resistance to apoptosis induced under nutrient deprivation and showed high viability even under nutrient deprivation.

3.2: Immunoblot Analysis (Western Blotting)

In order to examine whether apoptosis-related proteins are involved in apoptotic resistance which is the reason why the cancer stem cells show high viability under nutrient deprivation, each of p-MDA-MB-231, p-MCF-7, s-MDA-MB-231 and s-MCF-7 cell lines, cultured under glucose deprivation for 40 hours in the same manner as described in Example 2, was collected and subjected to immunoblot analysis. The collected cells were washed twice with chilled PBS (phosphate buffered saline) buffer, and lysed with RIPA buffer to isolate protein. For the next experiment, the amount of the isolated protein was measured by a BCA assay. 20 µg of the protein obtained from each of the cell lines was electrophoresed on 8-10% SDS-polyacrylamide gel and transferred to a PVDF membrane using electricity. The protein-transferred PVDP membranes were treated with 5% skim milk at room temperature for 1 hour, and then incubated with a primary antibody against each of caspase-3, caspase-7, Bcl-2 and beta-actin (control) at 4° C. for 16 hours. The PVDP membranes incubated with the antibodies were washed three times with TBST buffer to remove unbound primary antibodies, and were further incubated with HPR-conjugated secondary antibodies at room temperature for 1 hour. After completion of the incubation, the membranes were washed with TBST buffer to completely remove the secondary antibodies, and were treated with ECL buffer and incubated for 3 minutes, followed by exposure to Kodak X-OMAT AR Film. The results are shown in FIG. 4.

As shown in FIG. 4, in the s-MDA-MB231 cell line, the levels of activated caspase (cleaved form) 3 and 7 were all reduced, and in s-MCF-7, the levels of cleaved caspase 7 and 9 were all reduced. Such results suggest that, in the cancer stem cells under nutrient deprivation, the expressions of caspases, known as apoptosis markers, and p62 and LC3B, which are autophatic cell death-related substances, decreased, but the expression of Bcl-2 known as an anti-apoptosis marker increased, so that the viability of the cancer stem cells under nutrient deprivation increased.

3.3: Cell Cycle Analysis

In order to examine whether apoptosis of the cancer stem cells was induced under nutrient deprivation, each of p-MDA-MB-231, p-MCF-7, s-MDA-MB-231 and s-MCF-7 cell lines, cultured under glucose deprivation for 12 hours (early phase) and 40 hours (late phase) in the same manner as described in Example 2, was collected and subjected to cell cycle analysis. The collected cells were fixed with 70% ethanol, and then incubated in a PBS buffer containing 40 µg/mL of propidium iodide (PI) and 100 µg/mL of RNase for 30 minutes to stain the total DNA. Cell cycle analysis of the stained cells was performed using a FACS Calibur Flow Cytometer. The proportions of the cells in the G0/G1 stage, the S stage and the G2/M stages were measured using FACS and DNA software program (FlowJo). The results are shown in FIG. 5.

As shown in FIG. 5, in the early phase, there were no significant cell cycle-dependent changes in the ordinary stem cells and the cancer stem cells; however, in the late phase, the number of the cancer stem cells in the sub-G0/G1 stage significantly decreased. Such results suggest that apoptosis of the ordinary cancer cells in the late stage under nutrient deprivation increased, whereas apoptosis of the cancer stem cells under nutrient deprivation decreased.

From the above-described results, it could be seen that the cancer stem cells had resistance to apoptosis (anti-apoptosis) under nutrient deprivation, unlike the ordinary stem cells, and thus showed high viability even under nutrient deprivation.

EXAMPLE 4

Examination of Cause of Apoptotic Resistance of Cancer Stem Cells 4.1: Measurement of Level of Intracellular $Ca^{2+}$ In the case of many cells which undergo apoptosis, the concentration of intracellular calcium is not maintained, because events arise in which $Ca^{2+}$ is released from the endoplasmic reticulum to the cytosol or in which $Ca^{2+}$ flow into the cells through the plasma membrane. Thus, in order to examine whether $Ca^{2+}$ migration also occurs in cancer stem cells, cell lines under nutrient derivation were prepared in the same manner as described in Example 3, the level of intracellular $Ca^{2+}$ was measured using fura-2-AM which is a calcium indicator. The results are shown in FIG. 6.

As shown in FIG. 6, in the early phase, there was no significant difference in the level of intracellular $Ca^{2+}$ between the ordinary cancer cells and the cancer stem cells; however, in the late phase, the level of intracellular $Ca^{2+}$ in the cancer stem cells was higher than that in the ordinary cancer cells.

4.2: Analysis of Expression Level of CaMK-2α ($Ca^{2+}$/Calmodulin-dependent Kinase-2Alpha)

In order to examine the reason why the level of intracellular $Ca^{2+}$ in the cancer stem cells is higher than that in the ordinary cancer cells, the expression level of CaMK-2α was analyzed by Western blotting. The Western blotting was performed in the same manner as described in Example 3.2. The results are shown in FIG. 7.

As shown in FIG. 7, in both the early and late phases, the expression level of CaMK-2α in the cancer stem cells increased. From such results, it could be seen that the expression level of CaMK-2α in the cancer stem cells increased so that the level of $Ca^{2+}$ released from the endoplasmic reticulum into the cells under nutrient deprivation and metabolic energy stress would be controlled to a control level, and thus the cancer stem cells had resistance to apoptosis.

4.3: Examination of the Effect of Inhibition of Expression of CaMK-2α ($Ca^{2+}$/Calmodulin-Dependent Kinase-2Alpha)

In order to examine an effect which is obtained when the expression of CaMK-2α in the cancer stem cells, CaMK-2α siRNA purchased from Bioneer (Korea) was transfected into each cell line, thereby producing cancer cell stem cells in which expression of CaMK-2α was expressed. Furthermore, the expression level of CaMK-2α and the level of intracellular $Ca^{2+}$ were measured in the same manner as described in Examples 4.1 and 4.2. The results are shown in FIG. 8.

As shown in FIG. 8, in the cancer stem cells in which expression of CaMK-2α was inhibited, the level of $Ca^{2+}$ was not reduced. This result suggests that the expression of CaMK-2α in the cancer stem cells plays an important role in maintaining the level of intracellular $Ca^{2+}$.

In addition, using the cancer stem cells in which expression of CaMK-2α was inhibited, a TUNEL assay, immunoblot analysis and cell cycle analysis were performed in the same manner as described in Example 3. The results of the analyses are shown in FIGS. 9 to 11, respectively.

As shown in FIG. 9, the cancer stem cells under nutrient deprivation generally showed resistance to apoptosis; however, in the case of the cancer stem cells in which expression of CaMK-2α was inhibited using siRNA, apoptosis was induced to induce DNA fragmentation, like the case of the ordinary cancer cells.

As shown in FIG. 10, in the case of the cancer stem cells in which expression of CaMK-2α was inhibited, the levels of cleaved caspases increased again under nutrient deprivation and the expression level of Bcl-2 decreased, like the case of the ordinary cancer cells. In addition, it was shown that the levels of phosphorylated AKT (pAKT), phosphorylated IkB (p IkB) and phosphorylated NF-kB (p NF-kB) decreased and that IP3R (which is a calcium ion release channel) increased.

Such results suggest that, when the expression of CaMK-2α in the cancer stem cells is inhibited, the apoptotic resistance of the cancer stem cells under nutrient deprivation decreases and the cancer stem cells show results similar to those of ordinary cancer cells.

As shown in FIG. 11, in the case of the cancer stem cells in which expression of CaMK-2α was inhibited, the proportion of cells in the sub-G0/G1 stage of the late phase increased, like that in the ordinary stem cells, suggesting that apoptosis of the cancer stem cells under nutrient deprivation increased.

From the above results, it could be seen that the cancer stem cells under nutrient deprivation have resistance to $Ca^{2+}$ mediated apoptosis by increasing the expression level of CaMK-2α therein to regulate the level of intracellular $Ca^{2+}$ to a suitable level and that, when the expression of CaMK-2α in the cancer stem cells is inhibited, the cancer stem cells lose their resistance to apoptosis.

4.4: Examination of Relationship between PGC-1α (Peroxisome Proliferator Activated Receptor Gamma) and CaMK-2α

In order to examine whether PGC-1α whose expression is known to be regulated under nutrient deprivation has a relationship with resistance to $Ca^{2+}$ mediated apoptosis, a sh-PGC-1α vector (Origene) was transfected into the s-MDA-MB-231 cell line, thereby producing a cancer stem cell line in which expression of PGC-1α was inhibited. Immunoblot analysis of the produced cancer stem cell line was performed in the same manner as described in Example 3.2. The results are shown in FIG. 12.

A shown in FIG. 12, in the cancer stem cells in which expression of PGC-1α was inhibited, expression of CaMK-2α was also inhibited in the early and late phases, and the expression levels of Bcl-2, phosphorylated AKT and phosphorylated NF-kB were reduced under nutrient deprivation, like those in the ordinary cancer cells. In addition, it was shown that the expression level of the PMCA (plasma membrane $Ca^{2+}$ ATPase) protein known to be involved in extracellular release of $Ca^{2+}$ released from the endoplasmic reticulum was also reduced.

From the above results, it was found that the expression levels of CaMK-2α and PMCA in the cancer stem cells, in which expression of PGC-1α was inhibited, were inhibited. Thus, in order to examine whether the level of intracellular $Ca^{2+}$ changes, the level of $Ca^{2+}$ was measured in the same manner as described in Example 4.1. The results are shown in FIG. 13.

As shown in FIG. 13, in the early phase of nutrient deprivation, there was no significant difference; however, in the late phase, the level of intracellular $Ca^{2+}$ in the cancer stem cells, in which expression of PGC-1α, increased, and apoptosis of the cancer stem cells occurred.

The above results suggest that the expression level of PGC-1α in the cancer stem cells under nutrient deprivation increases to induce expression of CaMK-2α to thereby maintain the level of intracellular $Ca^{2+}$ at a suitable level so as to have resistance to $Ca^{2+}$ mediated apoptosis, and that PGC-1α plays an important role in increasing the viability of the cancer stem cells under nutrient deprivation.

EXAMPLE 5

Examination of the Role of PGC-1α in Cancer Stem Cells 5.1: Examination of Binding Relationship between PGC-1α and PMCA1

In order to examine the binding relationship between PGC-1α and PMCA1, an EMSA assay was performed using an EMSA kit according to the manufacturer's protocol. As a binding sequence (probe), "TTGACCTTTGGCCCA", which is the binding site sequence of the promoter of PMCA1, was used. The results are shown in FIG. 14.

As shown in FIG. 14, in the cancer stem cells in the late phase, the binding between HNF4α, PGC-1α and DNA (probe) increased, whereas the binding decreased in the ordinary cancer cells or the cancer stem cells in which expression of PGC-1α was inhibited. Such results suggest that, under nutrient deprivation, PGC-1α binds to HNF4α and binds to the promoter region of PMCA1 to thereby regulate the expression of PMCA1.

5.2: Examination of Binding Relationship between PGC-1α and PMCA2

In order to examine the relationship between PGC-1α and PMCA2, an EMSA assay was performed using an EMSA kit according to the manufacturer's protocol. As a binding sequence (probe), "CTGGAAATACCCC", which is the binding site sequence of the promoter of PMCA2, was used. The results are shown in FIG. 15.

As shown in FIG. 15, in the cancer stem cells under nutrient deprivation, the binding between NF-kB, PGC-1α and DNA (probe) increased, and when anti-p65 or anti-p50, which is an antibody against NF-kB, was added, the antibody did further bind to cause supershift. Such results suggest that, under nutrient deprivation, PGC-1α bind to NF-kB and binds to the promoter region of PMCA2 to thereby regulate the expression of PMCA2.

5.3: Examination of Relationship between PMCA and Nutrient Deprivation

In order to examine the change in expression level of PMCA under nutrient deprivation, each cell line under nutrient deprivation was cultured in the same manner as described in Example 2, and qRT-PCR was performed at varying time points during the culture period. From the cells collected at each time point, RNA was extracted using the RNeasy Mini Kit according to the manufacturer's protocol. Using 1 μg of the extracted RNA, qRT-PCR was performed using a one-step RT-PCR kit. The primer sequences used are shown in Table 1 below. The results are shown in FIG. 16. Furthermore, the same experiment as described above was performed using the cell line in which expression of CaMK-2α was inhibited, and the results are shown in FIG. 17.

TABLE 1

| Gene products | Forward primer | Backward primer |
|---|---|---|
| PMCA1 | TTTCCAAACACTGCTTCTCTTC | GGTCCACAGATGCATTACGA |
| PMCA2 | GTTTTAGGCACTTTTGTGGT | CTAATTCCTCCTCAGGTATT |
| PMCA3 | AGGCCTGGCAGACAACACCA | TCCCACACCAGCTGCAGGAA |
| PMCA4 | GAGCTTCCTGGATACCGATG | CTAGCTTGGCCACACTG |
| GAPDH | GGTAAGGTCGGAGTCAACGG | GAGGTCAATGAAGGGGTCATTG |

As shown in FIG. 16, in the s-MDA-MB-231 cell line, the expression levels of PMCA1 and PMCA2 increased as the culture time increased, and in the s-MCF-7 cell line, the expression levels of PMCA1, PMCA2 and PMCA4 increased. In addition, as shown in FIG. 17, in the cell line in which expression of CaMK-2α was inhibited, the expression level of PMCA under nutrient deprivation did not increase, unlike the case of the cancer stem cells.

5.4: Examination of the Effect of Inhibition of PMCA

In order to examine whether the calcium concentration regulatory ability of the cancer stem cells is changed when PMCA is inhibited under nutrient deprivation, the activity of PMCA and SERCA was inhibited by using caloxin (which is a calcium pump inhibitor) as an inhibitor of PMCA acting as $Ca^{2+}$-ATPase (calcium ATPase) in the plasma membrane and using thapsigargin which is an inhibitor of SERCA (sarco/endoplasmic reticulum $Ca^{2+}$-ATPase) acting as $Ca^{2+}$-ATPase (calcium ATPase), and then changes in the extracellular $Ca^{2+}$ concentrations of the cancer stem cells were measured. The results are shown in FIG. 18.

As shown in FIG. 18, when the cancer stem cells were treated with the calcium pump inhibitor caloxin, the extracellular calcium concentration of the cancer stem cells decreased, and the viability of the cells also decreased, like that of the ordinary cancer cells. However, it was shown that, when the cancer stem cells were treated with the SERCA inhibitor thapsigargin, the extracellular calcium concentration of the cancer stem cells was maintained at a high level, and the viability of the cells was also high. Such results suggest that when the activity of PMCA is inhibited by treatment with the calcium pump inhibitor, the viability of the cancer stem cells under nutrient deprivation can be reduced.

From the above-described results, it could be seen that, in the cancer stem cells under nutrient deprivation and metabolic energy exhaustion-associated endoplasmic reticulum stress, the expression of PGC-1α increases to promote the expression of CaMK-2α, and the cancer stem cells show resistance to $Ca^{2+}$ mediated apoptosis in which $Ca^{2+}$, acting as a coactivator of PMCA1 and PMCA2 to increase the expression of PMCA protein and released from the endoplasmic reticulum into the cytosol under nutrient deprivation, is released extracellularly so as to be accumulated in mitochondria to thereby induce apoptosis. In addition, from the above-described results, it could be expected that a combination of the calcium pump inhibitor with a method for inducing nutrient deprivation, which is generally used in anticancer therapy, can be used as an effective method for treating cancer stem cells.

EXAMPLE 6

Identification of Therapeutic Method Effective Against Cancer Stem Cells 6.1: Construction of Animal Models In order to identify a therapeutic method effective against cancer stem cells, breast cancer animal models were constructed. For construction of the breast cancer animal models, each of breast cancer cells (p-MDA-MB-231 and p-MCF-7) and breast cancer stem cell lines (s-MDA-MB-231 and s-MCF-7) was cultured in vitro, and the cultured cells were injected into the upper left flank of 5-6-week-old BALB/c nude mice at a density of $1.0 \times 10^7$ cells/mouse. Then, the mice were housed at 22° C. under a 12-hr light/12-hr dark cycle for 7 days while they were fed with water and feed, thereby constructing breast cancer animal models.

6.2: Immunohistochemistry

In order to examine whether the expressions of PMCA1, PMCA2, PGC-1α and CaMK-2α in the breast cancer animal models constructed in the same manner as described in Example 6.1 would be increased, immunohistochemistry was performed. Specifically, according to standard surgical pathology protocols, cancer tissue was collected from each mouse, and fixed with 10% neutral buffered formalin and embedded in paraffin. Then, tissue was sectioned to a thickness of 5 μm, followed by removal of the paraffin. The sectioned tissue was subjected to antigen retrieval in citrate buffer (pH 6) and treated with 3% hydrogen peroxide for 5 minutes, after which the tissue was treated with a 1:100 dilution of a primary monoclonal antibody against each of PMCA1, PMCA2, PGC-1α and CaMK-2α. Next, the tissue was counter-stained with haematoxylin, and then dried and observed. The stained portion was quantified using Meta-Morph 4.6 software. The results are shown in FIG. 19.

As shown in FIG. 19, the expressions of PMCA1, PMCA2, PGC-1α and CaMK-2α in the breast cancer animal models injected with the cancer stem cells were all increased.

6.3: Identification of Method for Treating Cancer Stem Cells

Breast cancer animal models, constructed in the same manner as described in Example 6.1, were divided into several groups, each consisting of 9 animals, and were injected intraperitoneally with a combination of 500 mg/kg of the glucose uptake inhibitor 2-deoxyglucose (2DG), 250 mg/kg of the biguanide-based drug metformin and 200 mg/kg of caloxin 2a1, once a day for 45 days, and the horizontal diameter (a) and vertical diameter (b) of cancer were daily measured using calipers, and the volume of the cancer was determined using the following equation: $4/3 \times B \times (a\ cm \times b\ cm)^3 \times \frac{1}{2}$. The results are shown in Table 2 and FIG. 20.

addition, in the case in which the cancer stem cells were treated with a combination of 2-deoxyglucose, caloxin and metformin, the cancer stem cells did not substantially grow.

The above results suggest that the use of the glucose uptake inhibitor and the biguanide-based drug induces nutrient deprivation and metabolic energy exhaustion-associated endoplasmic reticulum stress in cancer stem cells to thereby induce the expression of PMCA in the cancer stem cells, and that administration of the calcium pump inhibitor in combination with the glucose uptake inhibitor and the biguanide-based drug reduces the resistance of the cancer stem cells to $Ca^{2+}$-mediated apoptosis to thereby induce apoptosis of the cancer stem cells, indicating that it can provide an effective treatment method specific for cancer stem cells. Accordingly, it could be found that the use of the glucose uptake inhibitor and the biguanide-based drug in combination with the calcium pump inhibitor can effectively inhibit cancer stem cell-mediated cancer recurrence and/or metastasis, which is the limitation of conventional anticancer drugs.

TABLE 2

| | P231 | | | | | |
|---|---|---|---|---|---|---|
| Day | Control | 2DG | 2DG + caloxin | 2DG + metformin | 2DG + metfor. + calox. | S231 Control |
| 7 | 210.6 ± 33 | 219.1 ± 35 | 210.5 ± 24 | 210.7 ± 28 | 213.7 ± 22 | 210.5 ± 18 |
| 10 | 300.2 ± 38 | 302 ± 49 | 267.7 ± 22 | 224.4 ± 25 | 281.0 ± 25 | 277.3 ± 38 |
| 13 | 351.0 ± 28 | 337.6 ± 47 | 330.5 ± 39 | 239.4 ± 17 | 305.1 ± 25 | 481.2 ± 21 |
| 16 | 417.1 ± 34 | 388.6 ± 47 | 373.1 ± 36 | 259.0 ± 19 | 331.6 ± 44 | 594.6 ± 33 |
| 19 | 559.8 ± 38 | 440.7 ± 45 | 442.5 ± 53 | 296.4 ± 30 | 375.2 ± 57 | 743.0 ± 55 |
| 22 | 751.7 ± 60 | 513.4 ± 46 | 492.6 ± 59 | 332.6 ± 44 | 452.3 ± 64 | 878.2 ± 80 |
| 25 | 904.1 ± 96 | 621.4 ± 50 | 565.3 ± 84 | 399.2 ± 56 | 467.6 ± 66 | 1098.7 ± 98 |
| 28 | 1088.6 ± 87 | 834.4 ± 48 | 659.6 ± 126 | 484.3 ± 75 | 482.2 ± 74 | 1393.0 ± 97 |
| 31 | 1390.7 ± 56 | 1142.7 ± 50 | 707.8 ± 145 | 594.7 ± 102 | 490.0 ± 62 | 1896.8 ± 101 |
| 34 | 1791.3 ± 52 | 1547.4 ± 57 | 733.1 ± 177 | 714.8 ± 129 | 479.1 ± 57 | 2609.7 ± 106 |
| 37 | 2223.2 ± 85 | 1944.2 ± 64 | 767.8 ± 187 | 865.1 ± 160 | 463.2 ± 56 | 3403.7 ± 96 |
| 40 | 2704.1 ± 102 | 2359.0 ± 48 | 855.1 ± 240 | 1052.4 ± 169 | 482.1 ± 60 | 4118.2 ± 506 |
| 43 | 3425.1 ± 152 | 2866.1 ± 45 | 953.6 ± 228 | 1278.8 ± 175 | 535.2 ± 41 | 5265.3 ± 445 |

| | S231 | | | |
|---|---|---|---|---|
| Day | 2DG | 2DG + caloxin | 2DG + metformin | 2DG + metfor. + calox. |
| 7 | 228.5 ± 23 | 218.7 ± 24 | 221.5 ± 26 | 222.4 ± 32 |
| 10 | 277.6 ± 21 | 248.7 ± 27 | 239.8 ± 30 | 261.0 ± 54 |
| 13 | 474.4 ± 31 | 472.6 ± 35 | 268.1 ± 34 | 274.0 ± 56 |
| 16 | 539.2 ± 33 | 534.0 ± 28 | 307.0 ± 47 | 305.5 ± 62 |
| 19 | 638.2 ± 49 | 544.4 ± 29 | 360.4 ± 67 | 361.4 ± 60 |
| 22 | 777.0 ± 35 | 597.2 ± 73 | 440.5 ± 85 | 450.5 ± 57 |
| 25 | 911.6 ± 35 | 631.2 ± 93 | 544.2 ± 103 | 468.3 ± 60 |
| 28 | 1077.4 ± 68 | 655.6 ± 101 | 678.2 ± 130 | 496.3 ± 56 |
| 31 | 1290.6 ± 72 | 681.4 ± 101 | 816.5 ± 150 | 496.7 ± 56 |
| 34 | 1722.1 ± 69 | 723.6 ± 112 | 1066.0 ± 179 | 485.6 ± 54 |
| 37 | 2471.7 ± 81 | 829.5 ± 70 | 1448.0 ± 260 | 468.3 ± 59 |
| 40 | 3173.2 ± 105 | 927.2 ± 58 | 1805.5 ± 363 | 484.2 ± 57 |
| 43 | 4065.2 ± 119 | 1074.7 ± 85 | 2278.3 ± 527 | 536.2 ± 38 |

As shown in Table 2 above and FIG. 20, when the tumor volume was compared between the ordinary cancer cells and the cancer stem cells, it was shown that tumor growth in the case of the cancer stem cells was significantly fast. Furthermore, in the case in which the cancer stem cells were treated with 2-deoxyglucose alone, the tumor volume slightly decreased compared to that in the control group. In the case in which the cancer stem cells were treated with a combination of 2-deoxyglucose and metformin, the tumor volume slightly decreased, but in the case in which the cancer stem cells were treated with a combination of 2-deoxyglucose and caloxin, the tumor volume decreased 5-fold or more. In

EXAMPLE 7

Examination of Survival Mechanism of Cancer Stem Cells 7.1: Examination of Difference in Gene Expression between Cancer Cells and Cancer Stem Cells In order to examine the survival mechanism of cancer stem cells, each of p-MDA-MB-231, p-MCF-7, s-MDA-MB-231 and s-MCF-7 cell lines, cultured under glucose deprivation for 40 hours in the same manner as described in Example 2, was collected, and RNA was extracted from the collected cells in the same manner as described in Example 5.3 and was subjected to microarray analysis. The results are shown in FIG. 21.

As shown in FIG. 21, the SERCA2 gene acting as $Ca^{2+}$-ATPase (calcium ATPase) significantly increased in the cancer stem cells.

In addition, in order to examine the difference in expression of calcium regulatory genes, Western blotting was performed in the same manner as described in Example 3.2. The results are shown in FIG. 22. As shown in FIG. 22, in the cancer stem cells, the expression of SERCA2 increased, whereas the expression of IP3R decreased. Generally, it is known that, in cells under glucose deprivation, calcium ions are released into the cytosol through the IP3R channel, and when the release of calcium increases rapidly, apoptosis is ultimately induced, and during this induction of apoptosis, reuptake of calcium ions through SERCA2 may occur to inhibit apoptosis.

From the above results, it could be seen that, in the cancer stem cells, the expression of SERCA2 increased to promote reuptake of calcium, and the expression of IP3R was inhibited so that the release of calcium ions into the cytosol would also be inhibited.

As shown in FIG. 23, it could be seen that, due to the regulation of CaMK-2α, the expression of IP3R in the cancer stem cells was first inhibited so that the release of calcium ions would be inhibited, and then intracellular uptake of the released calcium ions through SERCA occurred to inhibit apoptosis so that the viability of the cells would increase even under nutrient depletion.

7.2: Examination of Change in CaMK-2α Signaling Mechanism

In order to examine the time-dependent change in the CaMK-2α signaling mechanism under nutrient deprivation, Western blotting was performed in the same manner as described in Example 3.2, and an EMSA assay was performed using p NF-kB in the same manner as described in Example 5.1. The results are shown in FIGS. 24 and 25.

As shown in FIG. 24, in the cancer stem cells, signaling substances of the CaMK-2α signaling mechanism were activated as nutrient deprivation progressed, unlike those in the ordinary stem cells.

Furthermore, as shown in FIG. 25, p NF-kB acted as a transcription factor to increase the expressions of the IP3R inhibitor Bcl-2 and SERCA2. Such results suggest that, when CaMK-2α signaling is activated, NF-kB is phosphorylated and activated, and due to the activated NF-kB, the expressions of Bcl-2 and CERCA2 are increased so that the reuptake of calcium ions increases, and the expression of IP3R is inhibited so that the release of calcium ions is inhibited.

7.3: Examination of the Effect of Inhibition of CaMK-2α Signaling Mechanism

In order to examine an effect which occurs when CaMK-2α signaling is inhibited, the cancer stem cells were treated with 10 μM of KN62 (1-[N,O-bis(5-isoquinolinesulfonyl)-N-methyl-L-tyrosyl]-4-phenylpiperazine) well known as an inhibitor of CaMK-2α, and then a TUNEL assay was performed in the same manner as described in Example 3.1 to examine apoptosis and DNA fragmentation. In addition, Western blotting was performed in the same manner as described in Example 3.2 to examine the expression of genes, and the viability of the cells was measured in the same manner as described in Example 2. The results are shown in FIGS. 26 to 28.

As shown in FIGS. 26 to 28, when CaMK-2α signaling in the cancer stem cells under nutrient deprivation was inhibited, phosphorylation of NF-kB did not occur, and for this reason, the expression of IP3R was inhibited while the expression of SERCA2 was increased so that the release of calcium ions would be increased, thereby inducing apoptosis. Such results suggest that an inhibitor of CaMK-2α can reduce the resistance of cancer stem cells to $Ca^{2+}$ mediated apoptosis to thereby induce apoptosis of the cancer stem cells, indicating that the use of the CaMK-2α inhibitor can provide an effective treatment method specific for cancer stem cells.

EXAMPLE 8

Examination of Characteristics of Cancer Stem Cell Animal Models

In order to examine the characteristics of animal models constructed in the same manner as described in Example 6, the produced breast cancer tissue was extracted from the animal models, and the tumor volume was measured. The results are shown in FIG. 29. In addition, the expression levels of proteins in the breast cancer tissue were analyzed by Western blotting and immunohistochemistry. The Western blotting was performed in the same manner as described in Example 3.2, and the immunohistochemistry was performed in the same manner as described in Example 6.2. The results are shown in FIGS. 30 and 31.

As shown in FIG. 29, the growth rate of tumors in the animal models based on the cancer stem cells was higher than that in the animal models based on the ordinary cancer cells.

In addition, as shown in FIGS. 30 and 31, the expression of IP3R in the animal models based on the cancer stem cells decreased and the expression of SERCA2 increased, compared to those in the animal models based on the ordinary cancer cells. Such results were consistent with the results of the in vitro experiment.

From such results, it could be seen that, in the case of the cancer stem cells, the CaMK-2α signaling mechanism could be activated in a poor environment in vivo to thereby inhibit the expression of IP3R and increase the expression of SERCA2, thereby inhibiting apoptosis induced by the release of calcium ions so as to increase the viability of cancer cells in vivo and promote cancer recurrence and/or metastasis. This suggests that a composition for treating cancer stem cells, which is effective against cancer stem cells, can be used as an effective therapeutic method that can overcome the limitation of conventional anticancer therapies to maximize the efficiency of treatment of cancer and inhibit cancer recurrence and/or metastasis.

Although the present disclosure has been described in detail with reference to the specific features, it will be apparent to those skilled in the art that this description is only of a preferred embodiment thereof, and does not limit the scope of the present invention. Thus, the substantial scope of the present invention will be defined by the appended claims and equivalents thereof.

INDUSTRIAL APPLICABILITY

As described above, the composition of the present invention can be used as an agent of treating cancer stem cells by effectively inducing apoptosis of the cancer stem cells. Accordingly, the composition of the present invention can be used as a pharmaceutical composition capable of effectively treating various cancer stem cells to effectively inhibiting cancer recurrence and/or metastasis.

The invention claimed is:

1. A method for inhibiting breast cancer stem cell growth in a subject, comprising administering a glucose uptake inhibitor to the subject and a calcium pump inhibitor, wherein the glucose uptake inhibitor is 2-deoxyglucose (2DG) and the calcium pump inhibitor is caloxin 2a1.

2. The method of claim 1, which further comprises administering a biguanide-based compound to the subject.

3. The method of claim 2, wherein the biguanide-based compound is one or more selected from the group consisting of metformin, phenformin, and buformin.

4. A method for treating breast cancer stem cells in a subject, comprising administering a glucose uptake inhibitor and a calcium pump inhibitor to the subject, wherein the glucose uptake inhibitor is 2-deoxyglucose(2DG) and the calcium pump inhibitor is caloxin 2a1.

5. The method of claim 4, which further comprises administering a biguanide-based compound to the subject.

6. The method of claim 5, wherein the biguanide-based compound is one or more selected from the group consisting of metformin, phenformin, and buformin.

* * * * *